(12) United States Patent
Magedov et al.

(10) Patent No.: US 9,334,280 B2
(45) Date of Patent: *May 10, 2016

(54) SYNTHETIC RIGIDIN ANALOGUES AS ANTICANCER AGENTS, SALTS, SOLVATES AND PRODRUGS THEREOF, AND METHOD OF PRODUCING SAME

(71) Applicant: New Mexico Technical Research Foundation, Socorro, NM (US)

(72) Inventors: Igor V. Magedov, Socorro, NM (US); Snezna Rogelj, Socorro, NM (US); Liliya V Frolova, Socorro, NM (US); Alexander Vladimir Kornienko, San Marcos, TX (US)

(73) Assignee: New Mexico Tech Research Foundation, Socorro, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/584,929

(22) Filed: Dec. 29, 2014

(65) Prior Publication Data

US 2015/0111906 A1    Apr. 23, 2015

Related U.S. Application Data

(63) Continuation-in-part of application No. 13/678,987, filed on Nov. 16, 2012, now Pat. No. 8,946,246.

(51) Int. Cl.
| | | |
|---|---|---|
| A01N 43/90 | (2006.01) |
| A61K 31/519 | (2006.01) |
| C07D 487/00 | (2006.01) |
| C07D 487/04 | (2006.01) |

(52) U.S. Cl.
CPC ............ C07D 487/04 (2013.01); A61K 31/519 (2013.01)

(58) Field of Classification Search
None
See application file for complete search history.

(56) References Cited

U.S. PATENT DOCUMENTS 8,946,246 B2 * 2/2015 Magedov ............. C07D 487/04
514/265.1

* cited by examiner

*Primary Examiner* — Jeffrey H Murray
(74) *Attorney, Agent, or Firm* — Jennifer S. Stachniak

(57) ABSTRACT

A compound having the Formula as follows:

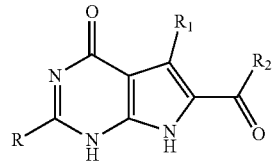

wherein R, $R_1$ and $R_2$ are selected from hydrogen, aryl, fused aryl, heteroaryl, saturated carbocylclic, partially saturated carbocyclic, saturated heterocyclic, partially saturated heterocyclic, $C_{1-10}$ alkyl, haloalkyl, alkenyl, alkynyl, arylalkyl, arylalkenyl, arylalkynyl, heteroarylalkyl, heteroarylalkenyl, alkenylalkyl, alkynylalkyl, carbocycloalkyl, heterocycloalkyl, hydroxyalkyl, aminoalkyl, carboxyalkyl, nitroalkyl, cyanoalkyl, acetamidoalkyl, and acyloxyalkyl. A process for the preparation thereof is also provided.

12 Claims, 9 Drawing Sheets

SYNTHETIC RIGIDIN ANALOGUES AS ANTICANCER AGENTS, SALTS, SOLVATES AND PRODRUGS THEREOF, AND METHOD OF PRODUCING SAME

The present application is a continuation-in-part application of patent application U.S. Ser. No. 13/678,987, filed Nov. 16, 2012.

BACKGROUND OF THE INVENTION

The present invention relates to synthetic rigidin analogues as anticancer agents, to salts, solvates and prodrugs thereof, and to a method of producing the same.

Cancer is the second leading cause of death in the United States. Cancer is a class of over 100 diseases that is characterized by unregulated, abnormal cell growth and proliferation. Anticancer agents are among the many different tools used to battle cancer. They can be used solely or in combination with other treatment regimens to fight the disease. Cancer rates are only expected to rise in the future as the average life-span continues to increase and thus the development of new anticancer agents is a top priority in the drug discovery community. Of particular importance is the vast number of new anticancer agents that have been derived from natural sources. Out of all new anticancer agents developed between 1981 and 2006, only about 20% have been totally synthetic and thus new natural compounds have served as excellent sources to create more potent, more selective agents than those that are currently used in the clinic.

Plant-Derived Natural Products as a Source of Anticancer Agents

Plants have a long history of use in the treatment of cancer, dating back as far as the 4$^{th}$ century BC when Hippocrates of Cos used oil obtained from the daffodil *Narcissus poeticus* L. to treat uterine tumors. Several plant-derived compounds are among the top anticancer agents used clinically; these include the vinca alkaloids, vinblastine (FIG. 1) and vincristine, and the taxanes taxol (FIG. 1) and its semi-synthetic analogue docetaxel. The vinca alkaloids are among the first plant-derived anticancer agents to advance to clinical usage and were first isolated in the 1950s from the Madagascar periwinkle plant.

Many other plant-derived compounds have been used as leads in the discovery of more potent and less toxic anticancer agents. Included among these are podophyllotoxin (FIG. 2), an antimitotic isolated from plants of the genus *Podophyllum*, and camptothecin (FIG. 2), a topoisomerase inhibitor isolated from *Camptotheca acuminate*, a tree extensively used in traditional Chinese medicine. Podophyllotoxin and camptothecin failed clinical trials themselves due to severe toxicity and poor water solubility but they both served as lead agents for the development of several clinically used anticancer drugs. These include three semisynthetic derivatives of podophyllotoxin teniposide, etoposide (FIG. 2), and etoposide phosphate, as well camptothecin analogues topotecan (FIG. 2) and irinotecan, all of which are now used clinically for the treatment of a variety of cancers.

Marine-Derived Natural Products as a Source for Anticancer Agents

In addition to plant-derived anticancer agents, a relatively new resource for the discovery of new anticancer drugs is marine natural compounds. These include natural products isolated from aquatic fungi, cyanobacteria, sponges, and tunicates. Cyanobacteria has been a rich source for new bioactive agents yielding approximately 300 new alkaloids, which are likely produced as toxins to ward off predators. Marine alkaloids derived from cyanobacteria have been well characterized and have shown various mechanisms of action against a variety of cancer cell lines, which include cell cycle arrest in $G_1$, targeting of actin or tubulin as well as histone deacetylase (HDAC) inhibition to list a few. Fungi generally produce a wide array of secondary metabolites that have shown promising anticancer potential, however the mode of action (MOA) of many of these alkaloids is not fully understood.

Marine sponges and tunicates have proven to produce some of the most interesting and useful marine-derived alkaloids to date. Many of the identified compounds have reached clinical trials and have very well defined MOAs, many of which are similar to those of the plant-derived natural products taxol and the camptothecins. These include hemiasterlin and its synthetic analogue E7974, which display a potent anti-tubulin activity, and the makaluvamines, which inhibit topoisomerase II (TOP II). Tunicates have long been known to be a major source of compounds for the treatment of cancer. Among these, the lamellarins and related pyrrole-derived alkaloids stand out as a group of marine alkaloids with promising biological activities, such as cytotoxicity, reversal of multidrug resistance (MDR), HIV-1 integrase inhibition, antibiotic activity, human aldose reductase inhibition, immunomodulation, antioxidant activity and others. In light of their fascinating novel structures, intriguing biological properties, and the difficulty in obtaining large quantities from natural sources, marine pyrrole-derived alkaloids have attracted considerable attention from organic and medicinal chemists. At present, several marine natural products are in clinical trials and one drug, trabectedin, was recently approved in Europe as the first ever marine-derived anticancer agent.

Rigidins as Potential New Anticancer Agents

Although there has been intense investigation into marine natural products, there are still many very potentially useful medicinal agents that have not been researched fully. Among these are the marine alkaloids rigidins A, B, C, D (FIG. 3) and E isolated from the tunicate *Eudistoma* cf. *rigida* found near Okinawa and New Guinea. The rigidins, due to their low availability from natural sources, are poorly investigated natural products even though they have several interesting biological properties. They are reported to exhibit cytotoxicity against cancer cell lines, while rigidin A was also shown to possess calmodulin antagonistic activity.

The rigidins incorporate the pyrrolo[2,3-d]pyrimidine ring system, which is considered a "privileged medicinal scaffold" (PMS). PMSs are molecular frameworks that are seemingly capable of serving as ligands for a diverse array of targets. The pyrrolo[2,3-d]pyrimidine ring system is analogous to the purine framework and, in addition to the rigidins, it is also a common motif in several other natural products, such as the nucleoside anticancer antibiotics tubercidin, toyocamycin, sangivamycin. Thus, the rigidins are an unexplored class of marine alkaloids that have a high potential for multiple biological activities.

Previously, the inventors discovered a three-component chemical reaction leading to an efficient synthesis of marine alkaloids rigidins (FIG. 4). Although these natural products had been reported to possess weak antiproliferative and calmodulin-antagonistic activities, their biological properties had been scarcely studied due to the insufficient quantity of material available from isolation and a lack of an efficient chemical synthesis. The inventors developed an efficient synthetic approach, which allowed them to prepare sufficient amounts of material for biological studies.

Evaluation of these synthetically prepared alkaloids against several cancer cell lines revealed very weak antiproliferative activities (>100 micromolar $IC_{50}$ values). The current discovery deals with the finding that an alteration of this reported synthetic methodology to a novel four-component reaction leads to the preparation of rigidin analogues possessing a previously unknown hypoxanthine-like skeleton (see the three representative, possible compounds in FIG. 5).

Furthermore, evaluation of these compounds against several cancer cell lines revealed a marked and unexpected potent antiproliferative effect at extremely low concentrations.

SUMMARY OF THE INVENTION

The present invention describes novel hypoxanthine-like analogues of marine alkaloids rigidins.

Accordingly, one aspect of the present application includes compounds of the Formula I:

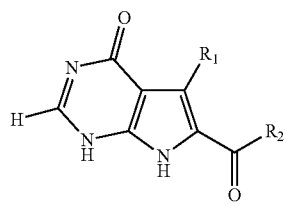

(I)

wherein $R_1$ and $R_2$ are selected from hydrogen, aryl, fused aryl, heteroaryl, saturated carbocyclic, partially saturated carbocyclic, saturated and partially saturated heterocyclic groups, C alkyl, haloalkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, and acyloxyalkyl.

In each alkyl, aryl, cycloalkyl or heteroaryl one or more available hydrogens can optionally be replaced by fluorine, and the resulting compound, or a pharmaceutically acceptable salt, solvate or prodrug thereof, are also within the scope of the present application.

In another embodiment the compounds of Formula I comprise an isotopic label (also known as an isotopic tracer or marker). Therefore, the present application also includes compounds of Formula I wherein one or more atoms are replaced with an isotopic label, such as $^2H$, $^3H$, $^{13}C$, $^{15}N$, $^{123}I$, $^{18}F$.

In another aspect of the application there is included a pharmaceutical composition comprising one or more compounds of Formula I, as defined above, and/or pharmaceutically acceptable salts, solvates and/or prodrugs thereof, and a pharmaceutically acceptable carrier, such as nanoparticles, liposomes, microbubbles, hydrocolloid beads, among many others.

In a further aspect of the application there is included a pharmaceutical composition comprising one or more compounds of Formula I, and/or pharmaceutically acceptable salts, solvates and/or prodrugs thereof, and a pharmaceutically acceptable carrier, to treat cancer.

In still a further aspect of the application there is included a method of treating cancer comprising administering an effective amount of one or more compounds of formula I as defined above, and/or pharmaceutically acceptable salts, solvates and/or prodrugs thereof, to a subject in need thereof.

A further aspect of the present application is a process for the preparation of compounds of Formula I, comprising:

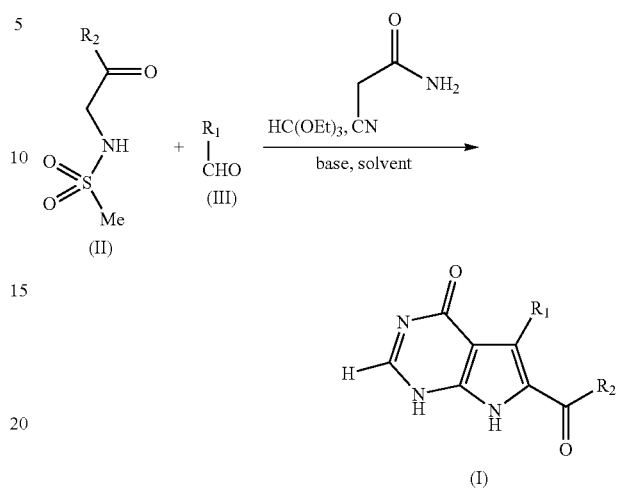

namely reacting a compound of the Formula II,

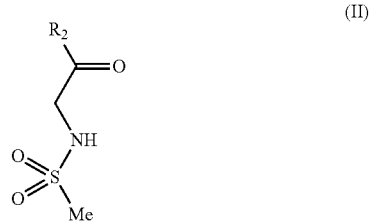

(II)

wherein $R_2$ is selected from hydrogen, aryl, fused aryl, heteroaryl, saturated carbocylclic, partially saturated carbocyclic, saturated heterocyclic, partially saturated heterocyclic, C alkyl, haloalkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, and acyloxyalkyl, with a compound of the Formula III,

(III)

wherein $R_1$ is selected from hydrogen, aryl, fused aryl, heteroaryl, saturated carbocylclic, partially saturated carbocyclic, saturated heterocyclic, partially saturated heterocyclic, C alkyl, haloalkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, and acyloxyalkyl, under conditions involving the use of. i.e. in the presence of, cyanoacetamide or its synthetic equivalents, and triethyl orthoformate or its synthetic equivalents, as well as a suitable base and solvent, to form compounds of Formula I. Examples of suitable solvents include ethanol, iso-propanol, butanol, acetonitrile, DMF, among others, and examples of suitable bases include K2CO3, Na2CO3, Cs2CO3, DBU, NaOH, KOH, among others.

Other features and advantages of the present application will become apparent from the following detailed description. It should be understood however that the detailed description and the specific examples, while indicating specific embodiments of this application, are given by way of illustration only, since various changes and modifications within the spirit and scope of the application will become apparent to those skilled in the art from this detailed description.

BRIEF DESCRIPTION OF THE DRAWINGS

The present application will now be described in greater detail, making reference to the accompanying drawings, in which.

DESCRIPTION OF SPECIFIC EMBODIMENTS

Figure 1:
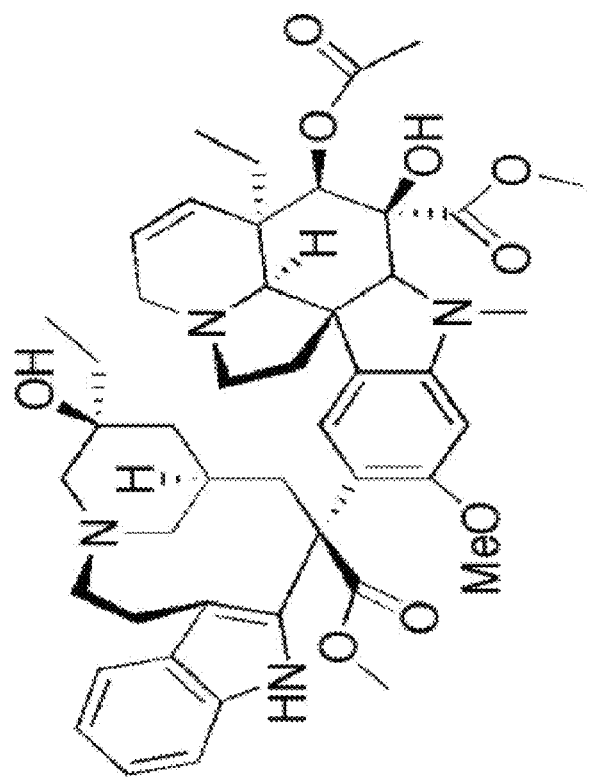
FIG. 1 shows structures of paclitaxel and vinblastine.
Figure 1:
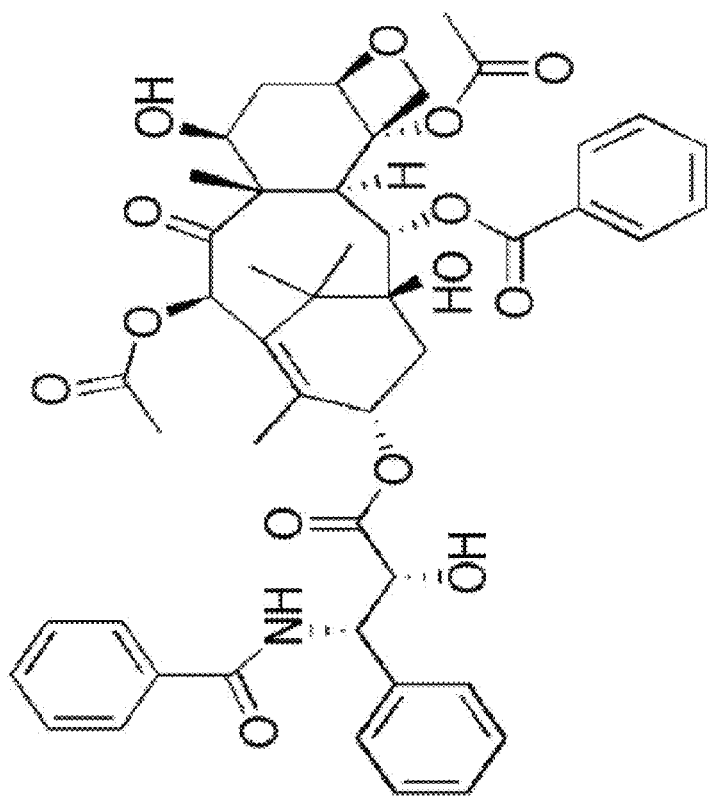
Figure 2:
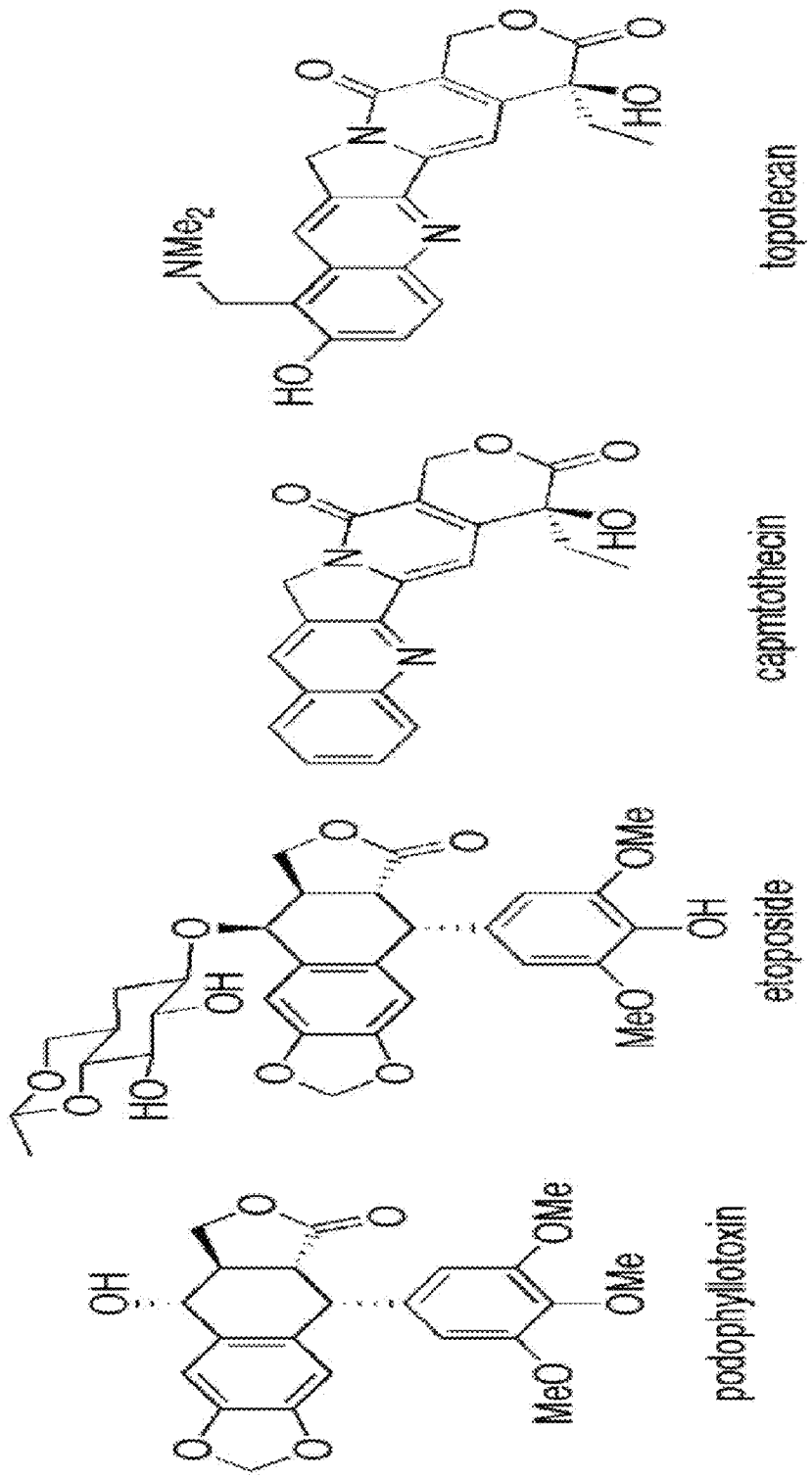
FIG. 2 shows representative structures of plant-derived anticancer agents and their clinically used derivitives.
Figure 3:
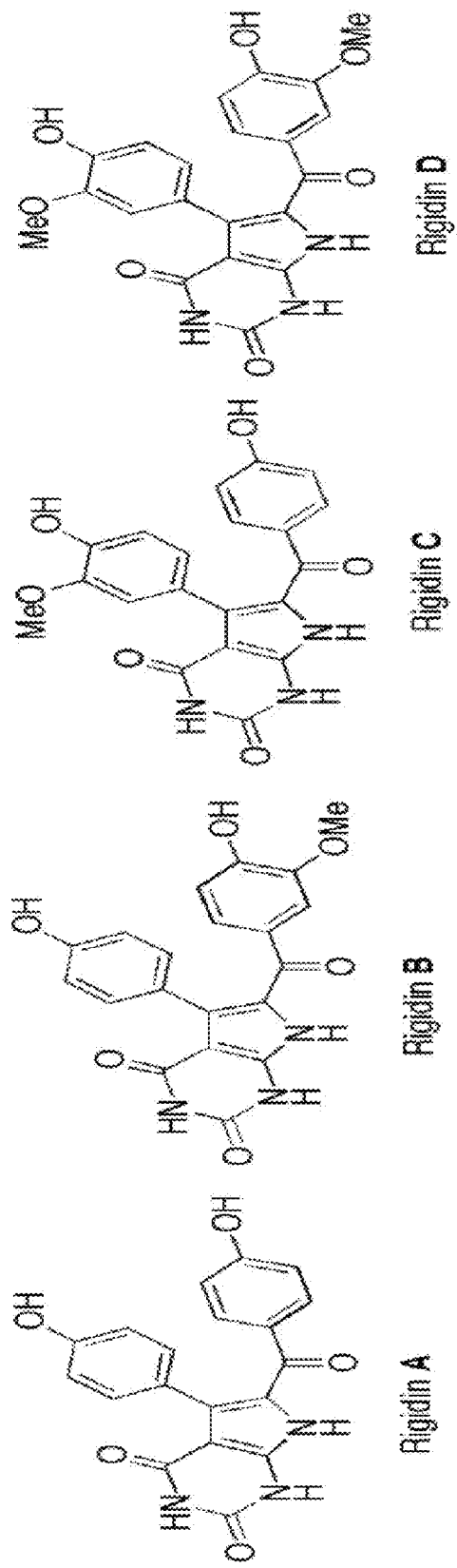
FIG. 3 shows structures of rigidins A, B, C and D.
Figure 4:
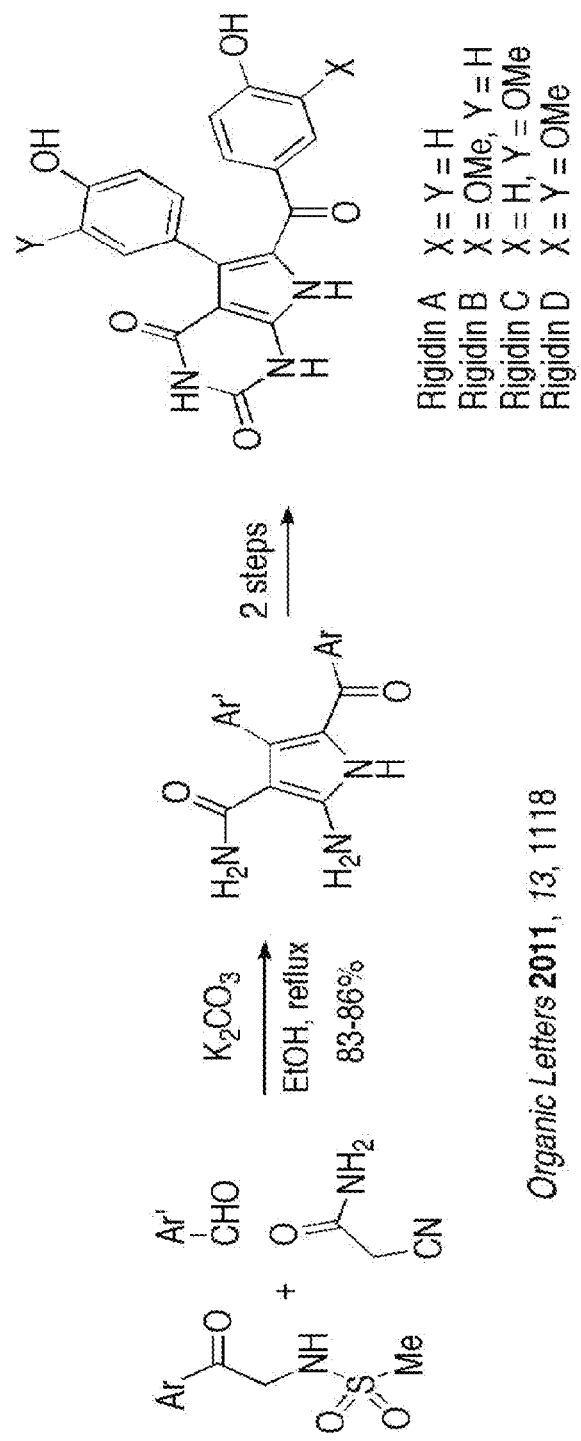
FIG. 4 illustrates a previously discovered synthetic pathway to natural rigidins.
Figure 5:
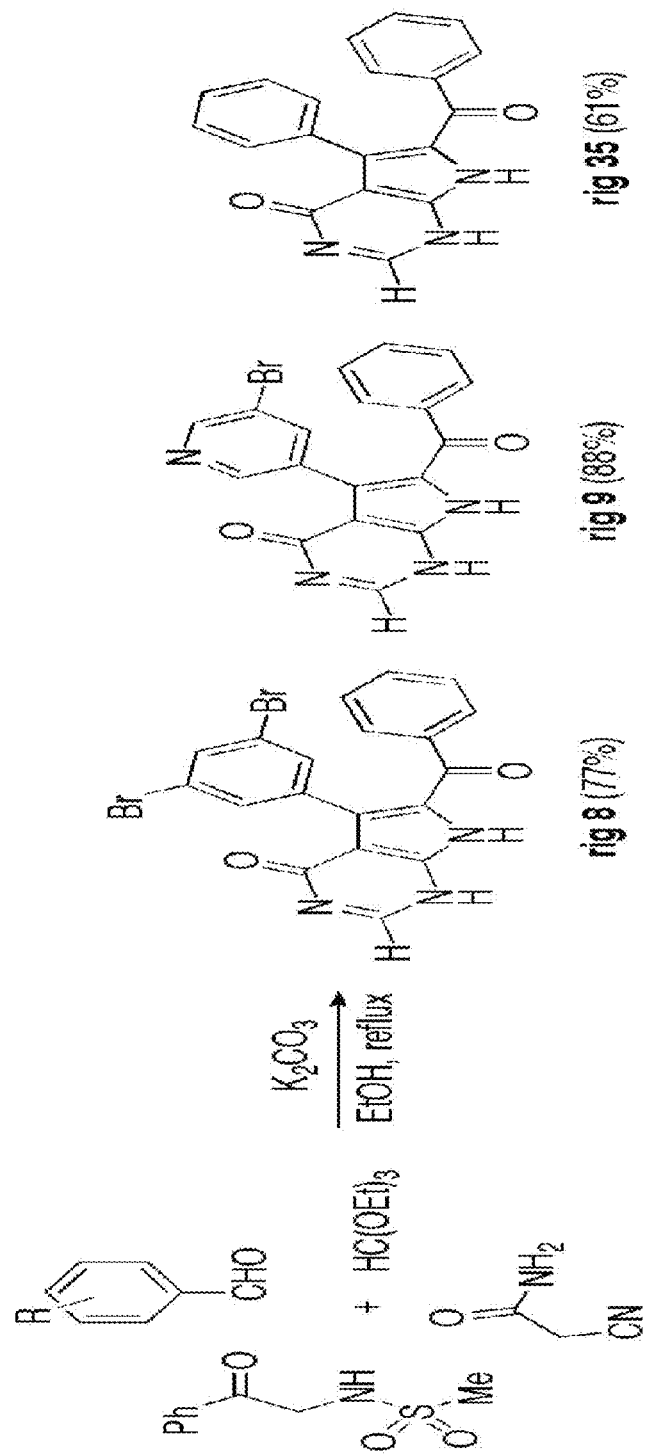
FIG. 5 shows an exemplary embodiment of the four-component reaction of the present application leading to the synthesis of hypoxamthine-like rigidin analogues.

Although most terms as used in the present application will be readily understandable by those of ordinary skill in the art, applicants would like to additionally emphasize the definitions for the terms solvate, prodrug and cancer. The term "solvate" as used in this application refers to a compound of this application, or a pharmaceutically acceptable salt thereof, wherein molecules of a suitable solvent are incorporated in the crystal lattice. Compounds of the present application also include prodrugs, which in general are functional derivatives of a compound of the present application that are readily convertible in vivo into the compound from which it is notionally derived. Prodrugs of the compounds of this application may be conventional esters formed with available hydroxyl or amino groups. Finally, the term "cancer" as used in the present application refers to a class of diseases or disorders characterized by uncontrolled division of cells and the ability of the cells to invade other tissues.

EXAMPLES

The following non limiting Examples are illustrative of the present application.

General procedure for the preparation of compounds of Formula I (1H-pyrrolo[2,3-d]pyrimidin-4(7H)-one): To a solution of N-(2-oxo-2-substituted)methanesulfonamide (0.676 mmol), selected or appropriate aldehyde (0.879 mmol) and cyanoacetamide (0.072 g, 0.879 mmol) in mixture of 2.5 ml EtOH and 2.5 ml RC(OEt)$_3$ (R=H or CH$_3$) was added anhydrous granulated K$_2$CO$_3$ (0.052 g, 0.372 mmol) in one portion. The mixture was purged with nitrogen for 5 min, and refluxed for 24 hours under the nitrogen atmosphere. The formation of pyrrole was controlled by TLC. After that the reaction temperature was increased to 150° C. and reaction mixture was heated during 10 hours again with simultaneous evaporation of ethanol. Then the mixture was cooled to room temperature, the formed precipitate was collected by filtration and washed on the filter with EtOH (2 mL) and diethyl ether. The mother liquor was evaporated and the residue subjected to column chromatography with MeOH/CH$_2$Cl$_2$=1/40 to 1/20 gradient.

Example 1

6-Benzoyl-5-(3,5-dibromophenyl)-1H-pyrrolo[2,3-d]pyrimidin-4(7H)-one (Rig8)

77%; $^1$H NMR (DMSO-d$_6$) δ: 13.01 (s, 1H), 12.10 (s, 1H), 8.06 (s, 1H), 7.51 (s, 1H), 7.46 (d, J=7.68 Hz, 2H), 7.41 (t, J=7.68 Hz, 1H), 7.36 (s, 2H), 7.23 (t, J=7.24 Hz, 2H); $^{13}$C NMR (DMSO-d$_6$) δ 187.9, 159.0, 149.9, 147.6, 138.0, 137.0, 133.3, 132.6, 131.9, 129.3, 128.6, 128.3, 124.0, 121.2, 107.0; HRMS m/z (ESI) calcd for C$_{19}$H$_{12}$Br$_2$N$_3$O$_2$ (M+H$^+$) 471.9296. found 471.9301.

Example 2

6-Benzoyl-5-(5-bromopyridin-3-yl)-1H-pyrrolo[2,3-d]pyrimidin-4(7H)-one (Rig9)

88%; $^1$H NMR (DMSO-d$_6$) δ: 13.01 (s, 1H), 12.12 (s, 1H), 8.35 (s, 1H), 8.31 (s, 1H), 8.05 (s, 1H), 7.81 (s, 1H), 7.46 (d, J=6.4 Hz, 2H), 7.38 (t, J=6.4 Hz, 1H), 7.21 (d, J=7.2 Hz, 2H); $^{13}$C NMR (DMSO-d$_6$) δ 187.7, 159.2, 150.2, 150.0, 148.3, 147.6, 140.8, 138.0, 132.6, 131.1, 129.6, 129.1, 128.4, 121.9, 119.0, 107.3; HRMS m/z (ESI) calcd for C$_{18}$H$_{11}$BrN$_4$NaO$_2$ (M+Na$^+$) 416.9963. found 416.9965.

Example 3

5-(3,5-Dibromophenyl)-6-(4-methoxybenzoyl)-1H-pyrrolo[2,3-d]pyrimidin-4(7H)-one (Rig 10)

60%; $^1$H NMR (DMSO-d$_6$) δ: 12.92 (s, 1H), 12.01 (s, 1H), 8.04 (s, 1H), 7.57 (s, 1H), 7.50 (d, J=8.36 Hz, 2H), 7.39 (s, 2H), 6.79 (d, J=8.36 Hz, 2H), 3.77 (s, 3H); $^{13}$C NMR (DMSO-d$_6$) δ 186.1, 162.5, 158.5, 149.1, 146.7, 136.6, 132.7, 131.4, 131.2, 129.9, 128.5, 122.3, 120.8, 113.3, 106.1, 55.5; HRMS m/z (ESI) calcd for C$_{20}$H$_{13}$Br$_2$N$_3$NaO$_3$ (M+Na$^+$) 523.9221. found 523.9221.

Example 4

6-(4-(Benzyloxy)benzoyl)-5-(3,5-dibromophenyl)-1H-pyrrolo[2,3-d]pyrimidin-4(7H)-one (Rig11)

61%; $^1$H NMR (DMSO-d$_6$) δ: 12.95 (s, 1H), 12.15 (s, 1H), 8.04 (s, 1H), 7.56 (m, 3H), 7.41 (m, 4H), 7.36 (m, 3H), 6.86 (d, J=7.92 Hz, 2H), 5.14 (s, 2H); $^{13}$C NMR (DMSO-d$_6$) δ 186.0, 161.6, 158.5, 149.1, 146.7, 136.6, 136.5 132.7, 131.4, 131.2, 130.0, 128.5, 127.9, 127.5, 122.3, 120.8, 114.1, 106.1, 69.4; HRMS m/z (ESI) calcd for C$_{26}$H$_{17}$Br$_2$N$_3$NaO$_3$ (M+Na$^+$) 599.9534. found 599.9532.

Example 5

5-(3,5-Dibromophenyl)-6-(4-fluorobenzoyl)-1H-pyrrolo[2,3-d]pyrimidin-4(7H)-one (Rig13)

56%; $^1$H NMR (DMSO-d$_6$) δ: 13.02 (s, 1H), 12.11 (s, 1H), 8.05 (s, 1H), 7.56 (s, 1H), 7.52 (t, J=6.4 Hz, 2H), 7.35 (s, 2H), 7.03 (t, J=8.0 Hz, 2H); HRMS m/z (ESI) calcd for $C_{19}H_{11}Br_2FN_3O_2$ (M+H+) 489.9202. found 489.9182.

Example 6

6-(4-Bromobenzoyl)-5-(3,5-dibromophenyl)-1H-pyrrolo[2,3-d]pyrimidin-4(7H)-one (Rig14)

54%; $^1$H NMR (DMSO-$d_6$) δ: 13.00 (s, 1H), 12.08 (s, 1H), 8.04 (s, 1H), 7.56 (s, 1H), 7.52 (d, J=8.06 Hz, 2H), 7.36 (s, 2H), 7.03 (d, J=8.66 Hz, 2H); $^{13}$C NMR (DMSO-$d_6$) δ 186.1, 165.7, 163.2, 159.1, 135.4, 133.6, 132.9, 132.7, 131.4, 124.3, 121.2, 115.2 114.9, 107.3; HRMS m/z (ESI) calcd for $C_{19}H_{11}Br_3N_3O_2$ (M+H$^+$) 549.8401. found 549.8395.

Example 7

6-(4-Methoxybenzoyl)-5-(3,4,5-trimethoxyphenyl)-1H-pyrrolo[2,3-d]pyrimidin-4(7H)-one (Rig19)

56%; $^1$H NMR (DMSO-$d_6$) δ: 11.97 (s, 1H), 8.01 (s, 1H), 7.46 (d, J=9.6 Hz, 2H), 6.71 (d, J=9.6 Hz, 2H), 6.51 (s, 2H), 3.71 (s, 3H), 3.56 (s, 6H), 3.32 (s, 3H); $^{13}$C NMR (DMSO-$d_6$) δ 187.0, 162.8, 159.3, 152.1, 149.8, 146.9, 136.6, 131.9, 128.4, 126.4, 113.6, 110.0 106.5, 60.4, 56.3, 56.0; HRMS m/z (ESI) calcd for $C_{23}H_{22}N_3O_6$ (M+H$^+$) 436.1509. found 436.1501.

Example 8

6-Benzoyl-5-(6-bromopyridin-2-yl)-1H-pyrrolo[2,3-d]pyrimidin-4(7H)-one (Rig30)

60%; $^1$H NMR (DMSO-$d_6$) δ: 13.05 (s, 1H), 12.17 (s, 1H), 8.09 (d, J=8.0 Hz, 1H), 8.03 (s, 1H), 7.61 (t, J=7.6 Hz, 1H), 7.49 (d, J=7.6 Hz, 2H), 7.40 (t, J=6.4 Hz, 1H), 7.23 (d, J=7.2 Hz, 2H), 7.19 (d, J=8.0 Hz, 2H); $^{13}$C NMR (DMSO-$d_6$) δ 188.5, 158.8, 152.7, 149.3, 146.8, 139.3, 138.7, 137.8, 132.2, 129.7, 128.5, 128.0, 125.4, 124.6, 122.1, 105.5; HRMS m/z (ESI) calcd for $C_{18}H_{12}BrN_4O_2$ (M+H$^+$) 395.0144. found 395.0125.

Example 9

6-Benzoyl-5-(3-iodo-4,5-dimethoxyphenyl)-1H-pyrrolo[2,3-d]pyrimidin-4(7H)-one (Rig31)

37%; $^1$H NMR (DMSO-$d_6$) δ: 12.85 (s, 1H), 12.00 (s, 1H), 8.02 (s, 1H), 7.40 (d, J=7.2 Hz, 2H), 7.33 (t, 1H), 7.16 (d, J=7.6 Hz, 2H), 7.07 (s, 1H), 6.82 (s, 1H), 3.58 (s, 6H); $^{13}$C NMR (DMSO-$d_6$) δ 188.1, 159.0, 150.9, 149.9, 147.6, 147.4, 138.2, 133.2, 132.2, 130.9, 129.2, 128.3, 128.1, 125.7, 117.2, 106.8, 91.3, 60.0, 56.1; HRMS m/z (ESI) calcd for $C_{21}H_{17}IN_3O_4$ (M+H$^+$) 503.0297. found 503.0280.

Example 10

6-Benzoyl-5-(3-bromo-4,5-dimethoxyphenyl)-1H-pyrrolo[2,3-d]pyrimidin-4(7H)-one (Rig32)

51%; $^1$H NMR (DMSO-$d_6$) δ: 12.87 (s, 1H), 12.01 (s, 1H), 8.04 (s, 1H), 7.41 (d, J=7.2 Hz, 2H), 7.34 (t, 1H), 7.16 (d, J=7.2 Hz, 2H), 6.95 (s, 1H), 6.77 (s, 1H), 3.59 (s, 6H); $^{13}$C NMR (DMSO-$d_6$) δ 188.0, 159.0, 152.0, 150.0, 147.5, 145.0, 138.2, 132.2, 130.2, 129.2, 128.2, 128.0, 127.4, 125.8, 116.3, 115.5, 106.9, 60.2, 56.3; HRMS m/z (ESI) calcd for $C_{21}H_{17}BrN_3O_4$ (M+H$^+$) 456.0382. found 456.0370.

Example 11

6-Benzoyl-5-(3-bromophenyl)-1H-pyrrolo[2,3-d]pyrimidin-4(7H)-one (Rig33)

54%; $^1$H NMR (DMSO-$d_6$) δ: 12.90 (s, 1H), 12.05 (s, 1H), 8.04 (s, 1H), 7.45 (d, J=7.32 Hz, 2H), 7.38 (t, J=6.96 Hz, 1H), 7.34 (s, 1H), 7.25 (d, J=7.76 Hz, 1H), 7.19 (m, 3H), 7.00 (t, J=7.08 Hz, 1H); $^{13}$C NMR (DMSO-$d_6$) δ 187.5, 158.5, 149.3, 146.9, 137.4, 134.8, 133.6, 132.0, 130.1, 129.4, 128.9, 128.8, 127.8, 127.7, 124.9, 120.1, 106.4; HRMS m/z (ESI) calcd for $C_{19}H_{13}BrN_3O_2$ (M+H$^+$) 394.0191. found 394.0183.

Example 12

6-Benzoyl-5-(3-chlorophenyl)-1H-pyrrolo[2,3-d]pyrimidin-4(7H)-one (Rig34)

61%; $^1$H NMR (DMSO-$d_6$) δ: 13.00 (s, 1H), 12.05 (s, 1H), 8.04 (s, 1H), 7.46 (d, J=7.4 Hz, 2H), 7.38 (t, J=6.2 Hz, 1H), 7.19 (m, 3H), 7.11 (d, J=7.52 Hz, 2H), 7.04 (t, J=7.48 Hz, 1H); $^{13}$C NMR (DMSO-$d_6$) δ: 187.6, 158.5, 149.4, 146.8, 137.5, 134.6, 132.0, 131.5, 130.7, 129.7, 128.9, 128.5, 127.7, 126.5, 125.0, 106.4; HRMS m/z (ESI) calcd for $C_{19}H_{13}ClN_3O_2$ (M+H$^+$) 350.0696. found 350.0694.

Example 13

6-Benzoyl-5-phenyl-1H-pyrrolo[2,3-d]pyrimidin-4(7H)-one (Rig35)

71%; $^1$H NMR (DMSO-$d_6$) δ: 12.79 (s, 1H), 12.01 (s, 1H), 8.02 (s, 1H), 7.43 (d, J=7.12 Hz, 2H), 7.33 (t, J=6.8 Hz, 1H), 7.15 (m, 4H), 7.04 (m, 3H); $^{13}$C NMR (DMSO-$d_6$) δ: 187.7, 158.6, 149.3, 146.7, 137.4, 132.4, 131.8, 131.1, 129.0, 127.7, 127.5, 126.8, 126.7, 126.6, 106.3; HRMS m/z (ESI) calcd for $C_{19}H_{14}N_3O_2$ (M+H$^+$) 316.1086. found 316.1087.

Example 14

6-Benzoyl-5-(3-iodophenyl)-1H-pyrrolo[2,3-d]pyrimidin-4(7H)-one (Rig36)

68%; $^1$H NMR (DMSO-$d_6$) δ: 12.90 (s, 1H), 12.09 (s, 1H), 8.04 (s, 1H), 7.42 (m, 5H), 7.25 (d, J=7.52 Hz, 1H), 7.19 (t, J=7.44 Hz, 2H), 6.87 (t, J=7.52 Hz, 1H); $^{13}$C NMR (DMSO-$d_6$) δ: 187.6, 158.5, 149.4, 146.9, 139.5, 137.4, 135.2, 134.6, 131.9, 130.4, 128.8, 128.7, 127.8, 125.0, 106.3, 93.0; HRMS m/z (ESI) calcd for $C_{19}H_{13}IN_3O_2$ (M+H$^+$) 443.0086. found 443.0080.

Example 15

6-Benzoyl-5-(2,6-dichlorophenyl)-1H-pyrrolo[2,3-d]pyrimidin-4(7H)-one (Rig40)

22%; $^1$H NMR (DMSO-$d_6$) δ: 13.01 (s, 1H), 12.05 (s, 1H), 8.02 (s, 1H), 7.47 (d, J=6.0 Hz, 2H), 7.34 (m, 1H), 7.20 (m, 3H), 7.12 (d, J=6.8 Hz, 2H); $^{13}$C NMR (DMSO-$d_6$) δ: 187.1, 158.0, 150.0, 147.6, 137.8, 135.3, 132.2, 132.0, 130.0, 128.2, 127.9, 127.5, 127.4, 120.2, 107.6; HRMS m/z (ESI) calcd for $C_{19}H_{12}Cl_2N_3O_2$ (M+H$^+$) 384.0307. found 384.0299

Example 16

6-Benzoyl-5-(pyridin-3-yl)-1H-pyrrolo[2,3-d]pyrimidin-4(7H)-one (Rig41)

61%; $^1$H NMR (DMSO-d$_6$) δ: 13.00 (s, 1H), 12.12 (s, 1H), 8.31 (s, 1H), 8.23 (m, 1H), 8.06 (s, 1H), 7.60 (d, J=7.72 Hz, 1H), 7.46 (d, J=7.12 Hz, 2H), 7.36 (t, J=6.88 Hz, 1H), 7.18 (t, J=7.24 Hz, 2H), 7.08 (m, 1H); $^{13}$C NMR (DMSO-d$_6$) δ 187.3, 158.6, 150.8, 149.5, 147.3, 147.0, 138.0, 137.3, 132.0, 129.2, 128.6, 127.9, 127.8, 123.0, 121.9, 106.7; HRMS m/z (ESI) calcd for $C_{18}H_{13}N_4O_2$ (M+H$^+$) 317.1039. found 317.1038.

Example 17

6-Benzoyl-5-(3-hydroxyphenyl)-1H-pyrrolo[2,3-d]pyrimidin-4(7H)-one (Rig42)

26%; $^1$H NMR (DMSO-d$_6$) δ: 12.72 (s, 1H), 11.97 (s, 1H), 9.08 (s, 1H), 7.98 (s, 1H), 7.45 (s, 2H), 7.34 (s, 1H), 7.17 (s, 2H), 676 (s, 1H), 6.65 (s, 1H), 6.51 (s, 1H), 6.43 (s, 1H); $^{13}$C NMR (DMSO-d$_6$) δ 188.4, 159.0, 156.5, 149.7, 147.1, 138.0, 134.1, 132.4, 129.4, 128.2, 128.0, 127.0, 122.6, 118.6, 114.2, 106.7; HRMS m/z (ESI) calcd for $C_{19}H_{14}N_3O_3$ (M+H$^+$) 332.1035. found 332.1032

Example 18

3-(6-Benzoyl-4-oxo-4,7-dihydro-1H-pyrrolo[2,3-d]pyrimidin-5-yl)benzonitrile (Rig43)

47%; $^1$H NMR (DMSO-d$_6$) δ: 12.99 (s, 1H), 12.11 (s, 1H), 8.06 (s, 1H), 7.59 (s, 1H), 7.51 (d, J=6.96 Hz, 2H), 7.44 (d, J=6.0 Hz, 2H), 7.38 (t, J=6.64 Hz, 1H), 7.26 (t, J=7.2 Hz, 1H), 7.19 (t, J=7.64 Hz, 1H); $^{13}$C NMR (DMSO-d$_6$) δ 187.3, 158.6, 149.4, 147.0, 137.4, 135.8, 134.5, 133.8, 131.9, 130.2, 129.0, 128.0, 127.8, 124.5, 118.6, 109.9, 106.5; HRMS m/z (ESI) calcd for $C_{20}H_{13}N_4O_2$ (M+H$^+$) 341.1039. found 341.1041.

Example 19

6-(4-Hydroxybenzoyl)-5-phenyl-1H-pyrrolo[2,3-d]pyrimidin-4(7H)-one (Rig45)

88%; $^1$H NMR (DMSO-d$_6$) δ: 12.66 (s, 1H), 11.93 (s, 1H), 10.17 (br.s, 1H), 7.99 (s, 1H), 7.40 (d, J=7.4 Hz, 2H), 7.22 (m, 2H), 7.11 (m, 3H), 6.52 (d, J=7.88 Hz, 2H); $^{13}$C NMR (DMSO-d$_6$) δ: 186.7, 161.5, 158.8, 148.9, 146.2, 132.7, 131.9, 131.0, 128.3, 127.9, 126.9, 126.5, 124.6, 114.6, 106.0; HRMS m/z (ESI) calcd for $C_{19}H_{13}KN_3O_3$ (M+H$^+$) 370.0594. found 370.0595.

Anticancer Activity (a) Cell Culture.

Human T-cell leukemia cell line Jurkat (ATCC TIB-152, E6-1 clone) was cultured in RPMI-1640 (Invitrogen) supplemented with 10% FBS (Invitrogen), 100 mg/L penicillin G, 100 mg/L streptomycin, 1.0 mM sodium pyruvate, 1.5 g/L sodium bicarbonate, and 4.5 g/L glucose (all from Sigma). Human cervical cancer cell line HeLa (ATCC S3) was cultured in DMEM (Invitrogen) supplemented with 10% FBS, 100 mg/L penicillin G, and 100 mg/L streptomycin. MCF-7 (human mammary carcinoma) cells were cultured in DMEM supplemented with 1.0 mM sodium pyruvate, 1% GlutaMax™-1 (Invitrogen), 100 µg/mL penicillin, 100 µg/mL streptomycin, and 10% FBS. Human uterine sarcoma MES-SA and MES-SA/Dx5 cells were cultured in RPMI-1640 medium supplemented with 10% FBS, 100 mg/L penicillin G and 100 mg/L streptomycin. All cells were incubated at 37° C. in a humidified atmosphere with 5% $CO_2$. The other cell lines were maintained in a similar fashion as previously described.

(b) MTT Assay.

To evaluate antiproliferative properties of the compounds of Formula I, mitochondrial dehydrogenase activities were measured using the MTT assay. The cell lines were prepared by trypsinizing and seeding 4×10 cells per well into microplates. All compounds were reconstituted in dimethyl sulfoxide (DMSO) at a concentration of either 100 mM or 25 mM prior to treatment. The cells were grown for 24 hrs before treatment at concentrations ranging from 0.004 to 100 microM and incubated for 48 hrs in 200 microL media. 20 microL of MTT reagent in serum free medium (5 mg/mL) was added to each well and incubated further for 2 hrs. Media was removed and the resulting formazan crystals were re-solubilized in 100 microL of DMSO and the optical density (OD) was measured using a Thermomax Molecular Device plate reader at a wavelength of 490 nm. The experiments were performed in quadruplicate and repeated at least twice for each compound per cell line. Cells treated with 0.1% DMSO were used as a negative control, while phenyl arsine oxide (PAO) was used as a positive killing control.

(c) Cell Cycle Assay

To assess the effects of the analogues on the cell cycle, cell cycle analysis was performed. 70-80% confluent HeLa cells were trypsinized and seeded at an initial density of 2×10$^5$ cell per well into 6 well plates in DMEM supplemented with 10% FBS, 100 mg/L penicillin G and 100 mg/L streptomycin. The cells were allowed to adhere overnight and before treatment with compounds of Formula I at concentrations ranging from 0.1 to 10 microM. After 24 hrs, the cells were washed 3× with DMEM, trypsinized, pelleted, and re-suspended in 200 microL of culture medium containing 10 microM (2 microL/mL) vybrant orange dye. The samples in the labeling solution were transferred into Falcon tubes and incubated in a water bath for 30 mins at 37° C. The samples were then analyzed using a Becton Dickinson FACscan flow cytometer with CellQuest software. A 488 nm laser was utilized using parameters that can be found in Appendix B; 10,000 events were collected for analysis. Cells treated with 0.1% DMSO were used as a negative control and cells treated with colchicine were used as a positive control.

(d) Apoptosis Assay.

2×10 Jurkat cells/mL were plated in 24 well plates, treated with the required compounds and incubated for the necessary number of hours. The cells were centrifuged at 400 G for 1 min. The supernatant was discarded and the cells were resuspended in 100 mL per sample of Annexin-V-FITC/propidium iodide solution in HHB (3 µL $CaCl_2$ (1.5 M) per mL HHB, 2 microL (10 mg/mL) propidium iodide (Sigma) per mL HHB and 20 microL Annexin-V-FITC (Southern Biotech, Birmingham, Ala.) per mL HHB). The samples in the labeling solution were transferred into Falcon tubes and incubated in a water bath at 37° C. for 20 min. The samples were then analyzed using a Becton Dickinson FACscan flow cytometer with CellQuest software. The results were tabulated as % of Annexin-V-FITC positive apoptotic cells.

(e) Results

MTT Assay: Antiproliferative Activity

The synthesized compounds of Formula I were evaluated for antiproliferative activity against a panel of cancer cell lines, including human HeLa cervical and MCF-7 breast adenocarcinomas. Many of the analogues exhibited nanomolar potency, characteristic of the clinically used anticancer agents and the results are shown in Table 1. Additionally, the selected compounds showed similar levels of activity against colon and head and neck cancer cell lines as well as cells derived from tumor metastases (Table 1A).

TABLE 1

Antiproliferative Properties of Compounds of Formula I.

| | $GI_{50}$ in vitro Values (microM)[a] | |
|---|---|---|
| | cervical adenocarcinoma HeLa | mammary gland adenocarcinoma MCF-7 |
| Rig8 | 0.095 ± 0.040 | 0.095 ± 0.010 |
| Rig9 | 0.080 ± 0.025 | 0.087 ± 0.020 |
| Rig10 | 0.30 ± 0.07 | 0.11 ± 0.035 |
| Rig11 | 0.40 ± 0.01 | 0.31 ± 0.01 |
| Rig12 | 0.4 ± 0.1 | 0.3 ± 0.07 |
| Rig13 | 6 ± 1 | 0.80 ± 0.01 |
| Rig14 | 2 ± 1 | 0.6 ± 0.1 |
| Rig19 | >100 | 7 ± 1 |
| Rig25 | 48 ± 8 | 33 ± 4 |
| Rig27 | 5 ± 1 | 6 ± 1 |
| Rig30 | 0.15 ± 0.05 | 0.135 ± 0.075 |
| Rig31 | 8 ± 1 | 40 ± 4 |
| Rig32 | 7 ± 1 | 10 ± 5 |
| Rig33 | 0.13 ± 0.05 | 0.06 ± 0.02 |
| Rig34 | 0.10 ± 0.07 | 0.06 ± 0.02 |
| Rig35 | 0.035 ± 0.007 | 0.040 ± 0.024 |
| Rig36 | 0.2 ± 0.1 | 0.150 ± 0.060 |
| Rig38 | 0.065 ± 0.010 | 0.070 ± 0.025 |
| Rig40 | 4.88 ± 0.07 | 2.20 ± 0.3 |
| Rig41 | 0.888 ± 0.061 | 1.26 ± 0.18 |
| Rig42 | 0.86 ± 0.06 | 1.10 ± 0.12 |
| Rig43 | 0.187 ± 0.009 | 0.251 ± 0.017 |
| Rig44 | 0.045 ± 0.004 | 0.053 ± 0.005 |
| Rig45 | 0.303 ± 0.005 | 0.261 ± 0.050 |

[a]Concentration required to reduce the viability of cancer cells by 50% after 48 h of treatment with indicated compounds relative to DMSO control ± SD from two independent experiments, each performed in 8 replicates, determined by MTT assay.

TABLE 1A

Antiproliferative Properties of Compounds of Formula 1

| | colon cancer | | | | head and neck cancer | | head and neck metastases | |
|---|---|---|---|---|---|---|---|---|
| compound | GEO | HCT8 | SW480 | SW620 | UM-SCC10A | UM-SCC22A | UM-SCC10B | UM-SCC22B |
| Rig8 | ND[b] | ND[b] | ND[b] | ND[b] | 90 | 110 | 100 | 20 |
| Rig9 | ND[b] | ND[b] | ND[b] | ND[b] | 90 | 120 | 130 | 20 |
| Rig35 | 0.008 | <0.001 | <0.001 | <0.001 | ND[b] | ND[b] | ND[b] | ND[b] |

[a]Concentration required to reduce the viability of cells by 50% after a 48 h treatment with the indicated compounds relative to a DMSO control, as determined by the MTT assay.
[b]ND = not determined Importantly, glioma, melanoma, non-small-cell lung, and a number of other types of cancer known to be associated with dismal prognoses. Thus, the rise in incidence of gliomas and melanomas has not been paralleled by improved therapeutic options over the years. New types of drugs are, therefore, urgently needed to combat cancers that are poorly responsive to current therapies. Therefore, the most potent compounds Rig8, Rig9 and Rig35 were tested against human U373 glioblastoma (GBM, from astroglial origin), human Hs683 anaplastic oligodendroglioma, human A549 non-small-cell-lung cancer (NSCLC), human SKMEL-28 and mouse B16F10 melanoma cell lines and the results are shown in Table 2. Thus, the discovery that compounds of Formula I show potent activity against cell lines representing cancers with dismal prognoses is extremely promising.

TABLE 2

Antiproliferative properties of most potent compounds of Formula I against cancer cell lines representing cancers with dismal prognoses

| | $GI_{50}$ in vitro values (microM)[a] | | | | |
|---|---|---|---|---|---|
| | glioma | | carcinoma | melanoma | |
| | U373 | Hs683 | A549 | SKMEL-28 | B16F10 |
| Rig8 | 0.03 | 0.02 | 0.03 | 0.02 | 0.05 |
| Rig9 | 0.03 | 0.02 | 0.02 | 0.02 | 0.04 |
| Rig35 | <0.01 | 0.01 | 0.02 | <0.01 | 0.01 |

[a]Concentration required to reduce the viability of cancer cells by 50% after 48 h of treatment with indicated compounds relative to DMSO control ± SD from two independent experiments, each performed in 8 replicates, determined by MTT assay.

Although drugs like taxol and vinblastine are very successful at treating a tumor initially, it is often the case that when there is a recurrence, the tumor is then unresponsive to these drugs due to overexpression of p-gp. The cells of such tumors are referred to as multidrug resistant (MDR). Thus, we assessed the compounds of Formula I for antiproliferative activity in an MDR cancer cell line. This was done using the uterine sarcoma cells, MES-SA/Dx5, which overexpress p-gp. The parental drug-responsive MES-SA cell line was used as control.

The data for Rig8 and Rig35 as well as controls taxol and vinblastine are shown in Table 3. As can be seen, there is only a small variation in the sensitivities of the parental and MDR cell lines using Rig8 and Rig35, while taxol and vinblastine are ca. 1000 times less potent against the MDR cells compared with the parental MES-SA uterine sarcoma cells. These results suggest that compounds of Formula I are not sensitive to the action of p-gp and thus have significant clinical potential.

TABLE 3

Antiproliferative Effect of Selected Compounds of Formula I Against MDR Cells

| | $GI_{50}$ in vitro Values (nM) | |
|---|---|---|
| | MES-SA | MES-SA/Dx5 |
| Taxol | 7 ± 1 | 9800 ± 283 |
| Vinblastine | 6 ± 1 | 5000 ± 1414 |
| Rig8 | 81 ± 6 | 394 ± 10 |
| Rig35 | 30 ± 4 | 70 ± 4 |

Cell Cycle Assay

Figure 6:
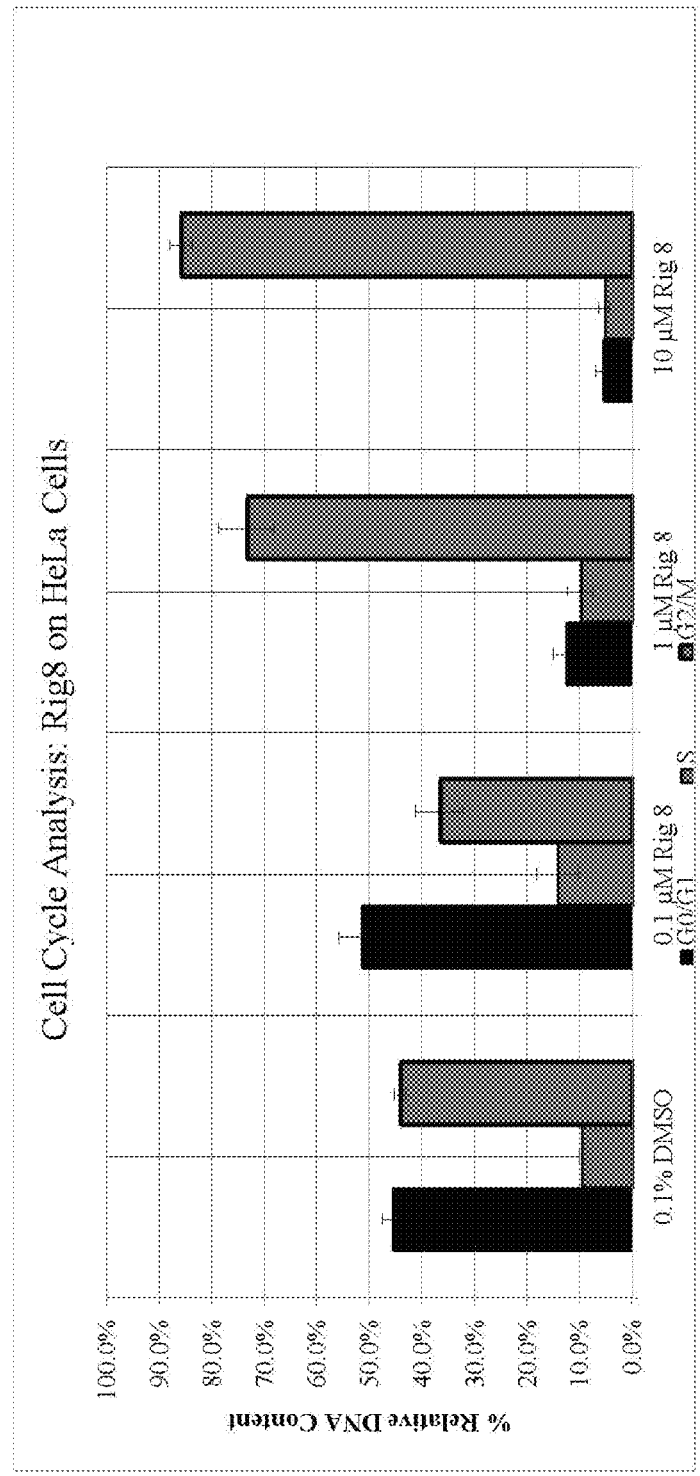
FIG. 6 is a graph showing cell cycle analysis using HeLa cells treated for 24 hrs with Rig8; error bars represent the standard deviation between triplicate experiments.

In further anticancer evaluation of compounds of Formula I cell cycle analysis was performed using the cell permeable DNA binding dye Vybrant Orange. In a normal population, cells are distributed among the three major phases of the cell cycle, $G_0/G_1$ in which there is one set of paired chromosomes per cell (2n), followed by the S or synthesis phase in which DNA is synthesized in preparation for division (there is a variable amount of DNA present during this phase) and finally $G_2/M$ phase in which the chromosomes of each cell have now been duplicated (4n). This DNA content can be measured using fluorescent DNA selective probes such as Vybrant Orange that produce signals that are proportional to DNA mass per cell. This dye interacts with double stranded DNA (dsDNA) in living cells and becomes fluorescent upon binding and thus can be used to track DNA content as cells progress through the various phases of the cell cycle using flow cytometry. Cell cycle analysis was performed on HeLa cells using Rig8 at various concentrations above and below the respective $GI_{50}$. Since colchicine is a known antimitotic drug, it was utilized as a positive control, while HeLa cells treated with 0.1% DMSO were used as a negative control. FIG. 6 illustrates the results of this analysis using Rig 8 on HeLa cells.

As can be seen in FIG. 6 and Table 4, Rig8 caused dose-dependent cell cycle arrest in the $G_2/M$ phase using the HeLa cell line.

TABLE 4

Flow Cytometric Cell Cycle Analysis of Rig8 Using HeLa Cells.

| Compound | % Relative DNA Content[a] | | |
|---|---|---|---|
| | $G_0/G_1$ | S | $G_2/M$ |
| 0.1% DMSO | 45.5 ± 1.9 | 9.6 ± 0.4 | 44.2 ± 1.1 |
| Colchicine(0.1 μM) | 28.7 ± 1.2 | 15.7 ± 1.9 | 53.6 ± 1.3 |
| Rig8 (10 μM) | 5.6 ± 2.2 | 5.3 ± 2.4 | 85.9 ± 2.1 |
| Rig8 (1 μM) | 12.7 ± 2.2 | 9.7 ± 2.4 | 73.4 ± 5.3 |
| Rig8 (0.1 μM) | 51.5 ± 4.3 | 14.1 ± 3.9 | 36.6 ± 4.6 |

[a]% Relative DNA content ± SD after 24 h treatment of HeLa cells with indicated compounds from two independent experiments each performed in triplicate.

Apoptosis Assay

Figure 7:
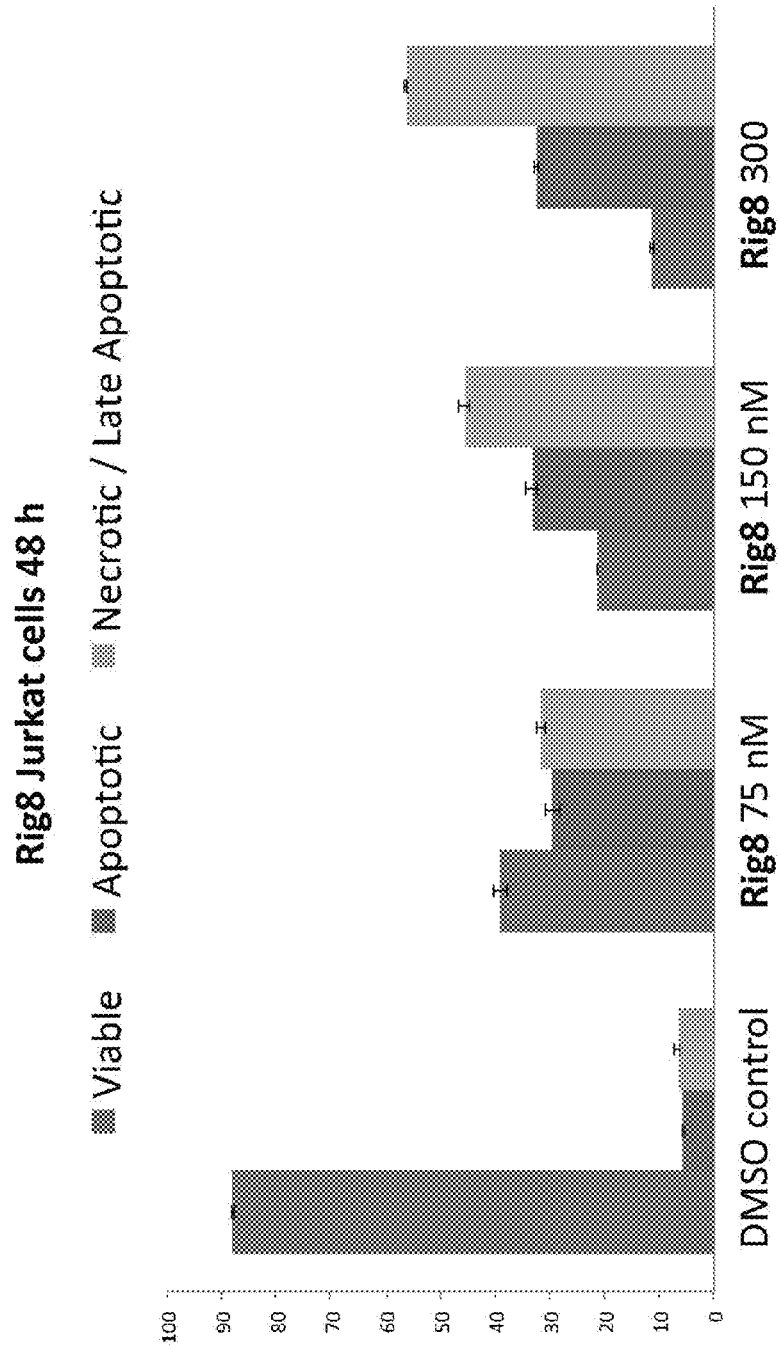
FIG. 7 illustrates apoptosis induction in RIG 8.

It has been reported that the anticancer efficacy of many currently used chemotherapeutic agents is strongly correlated with their ability to induce apoptosis in cancer cells and, therefore, many primary screens for novel anticancer leads are now based not on identification of compounds with antiproliferative activity, but rather on their apoptosis inducing properties. Therefore, compounds of Formula I were tested for their ability to induce apoptosis in Jurkat cells in a flow cytometric Annexin-V/propidium iodide assay and the percentages of apoptotic cells after 48 hours of treatment by Rig8 at different concentrations are shown in FIG. 7.

Figure 8:
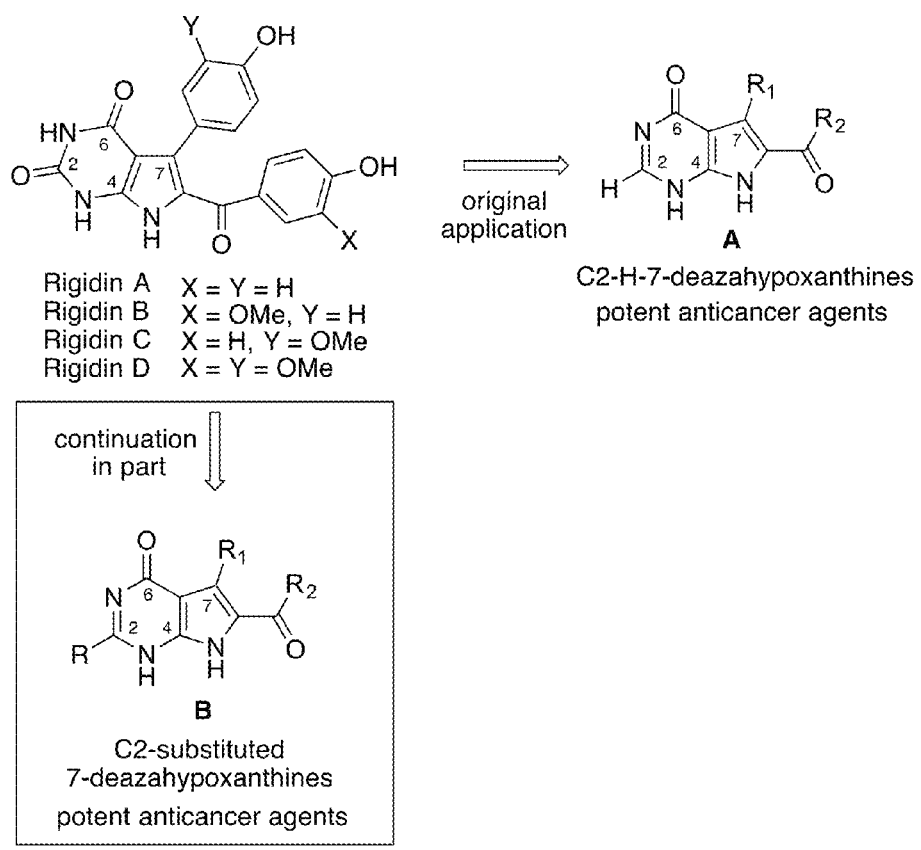
FIG. 8 illustrates structures of rigidins A, B, C, D, their synthetic analogues based on 7-deazahypoxanthine (A) and novel C2-substituted 7-deazahypoxanthines (B)

As discussed in detail above, novel analogues of marine alkaloid rigidins were prepared utilizing new synthetic methods developed for the construction of the pyrrolo[2,3-d]pyrimidine ring system. The synthesized compounds exhibited submicromolar to nanomolar antiproliferative potencies against drug resistant cells, such as glioblastoma, melanoma and non-small-cell lung cancer. The compounds described above include compounds in which the position C2 remained unsubstituted (A, FIG. 8). Thus, it was further decided to prepare a series of C2-substituted-deazahypoxanthines (B, FIG. 8) and evaluate these compounds for anticancer activities. It was further discovered that such compounds also possess potent antiproliferative activities against a number of cancer cell lines.

Results (a) Synthesis and SAR of C2-Substituted-7-Deazahypoxanthines

To develop synthetic access to the C2-substituted 7-deazahypoxanthines B, a previously discovered multicomponent reaction (MCR) of sulfonamidoacetophenones with aldehydes and cyanoacetamide was utilized to prepare pyrrole 1 (Table 5). This was followed by the pyrimidine ring closure using the reaction of 1 with a variety of aromatic and aliphatic esters catalyzed by sodium ethoxide in ethanol that was reported for a related purine system. The desired 7-deazahypoxanthines 2-17 were obtained in variable but acceptable yields (Table 5), given that in most cases these products precipitated after the acidification of the reaction mixtures and required no further purification.

TABLE 5

Synthesis and antiproliferative activities of C2-substituted-7-deazahypoxanthines 2-17

| # | structure | % yield | cell viability[a] $GI_{50}$, μM | |
|---|---|---|---|---|
| | | | HeLa | MCF-7 |
| 2 | 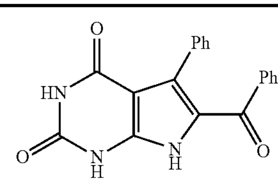 | NA[b] | >50 | >50 |
| 3 | 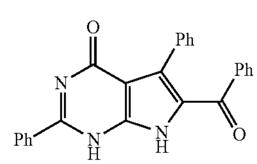 [SMILES: O=C(c1ccccc1)c1[nH]c2[nH]c(-c3ccccc3)nc(=O)c2c1-c1ccccc1] | 41 | >50 | >50 |

TABLE 5-continued

Synthesis and antiproliferative activities of C2-substituted-7-deazahypoxanthines 2-17

| # | Structure | Yield | HeLa | MCF-7 |
|---|---|---|---|---|
| 4 | 2-(pyridin-3-yl) derivative | 33 | >50 | >50 |
| 5 | 2-(pyridin-2-yl) derivative | 18 | 2.7 ± 0.2 | 2.5 ± 0.3 |
| 6 | 2-(furan-2-yl) derivative | 58 | 18.4 ± 1.8 | 23.1 ± 0.5 |
| 7 | 2-(EtO₂C) derivative | 41 | >50 | >50 |
| 8 | 2-(EtO) derivative | NA$^c$ | 11.1 ± 0.4 | 10.4 ± 0.8 |
| 9 | 2-(isopropyl) derivative | 21 | 9.1 ± 0.3 | 8.3 ± 0.8 |
| 10 | 2-(CH₂CH₂CO₂Et) derivative | 60 | 0.78 ± 0.05 | 0.93 ± 0.07 |
| 11 | 2-(n-butyl) derivative | 42 | 0.34 ± 0.01 | 0.23 ± 0.01 |
| 12 | 2-ethyl derivative | 72 | 0.92 ± 0.11 | 1.1 ± 0.1 |
| 13 | 2-methyl (H₃C) derivative | 49 | 0.029 ± 0.001 | 0.035 ± 0.003 |
| 14 | 2-(FH₂C) derivative | 35 | 3.0 ± 0.2 | 3.2 ± 0.2 |
| 15 | 2-(F₂HC) derivative | 47 | 5.1 ± 0.2 | 4.2 ± 0.5 |
| 16 | 2-(F₃C) derivative | 66 | 21.5 ± 0.4 | 21.1 ± 1.1 |
| 17 | 2-(pent-4-ynyl) derivative | 70 | 0.022 ± 0.002 | 0.045 ± 0.001 |

$^a$Concentration required to reduce the viability of cells by 50% after a 48 h treatment with the indicated compounds relative to a DMSO control ± SD from two independent experiments, each performed in 4 replicates, as determined by the MTT assay.
$^b$Synthesized using the method described in ref. 13.
$^c$Obtained as a side product of the reaction of 1 with CO(OEt)₂.

The obtained compounds were evaluated for antiproliferative activities using the HeLa cell line as a model for human cervical adenocarcinoma and MCF-7 cells as a model for breast adenocarcinoma. The cells were treated with each compound for 48 h, and cell viability was assessed using the MTT method (Table 5). The results revealed that in comparison with the rigidin-related 7-deazaxanthine 2, containing the carbonyl group at C2, most of the C2-substituted 7-deazahypoxanthines showed antiproliferative activity. The activity was found to be double to single digit micromolar for C2-aryl (5, 6), C2-OEt (8) and branched C2-alkyl (9). The linear C2-alkyl derivatives 10-12 showed submicromolar potency and the C2-methyl as well as C2-pentynyl compounds 13 and 17 were nanomolar.

(b) MCR-Based Synthesis and SAR of C2-Methyl-7-Deazahypoxanthines

Potent activity of the C2-methyl analogue 13 led to further exploration of C2-methyl compounds by varying the aldehyde-derived C7 aromatic group. To facilitate the synthesis of such compounds, a new 4-component cyclocondensation of methylsulfonamidoacetophenone, cyanoacetamide and triethyl orthoacetate with various aldehydes was developed (Table 6). In this reaction, the entire pyrrolo[2,3-d]pyrimidine skeleton is assembled in one step and its success depended on an optimized temperature regime, in which the reaction was first kept at 90° C. to allow for a clean formation of intermediate aminopyrroles (similar to 1 in Table 5), and then at 150° C. to bring the fourth component orthoacetate into the process, leading to closure of the pyrimidine portion of the molecule.

TABLE 6

MCR-based synthesis and antiproliferative activities of C2-methyl-7-deazahypoxanthines 13 and 18-23

| # | structure | % yield | GI$_{50}$ in vitro Values (μM)$^a$ | | | |
|---|---|---|---|---|---|---|
| | | | HeLa | MCF-7 | U-87 | A549 |
| 13 | 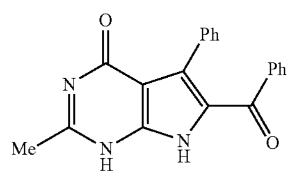 [SMILES: Cc1nc(=O)c2c(-c3ccccc3)c(C(=O)c3ccccc3)[nH]c2[nH]1] | 40 | 0.029 ± 0.001 | 0.035 ± 0.003 | 0.077 ± 0.002 | 0.25 ± 0.01 |
| 18 | 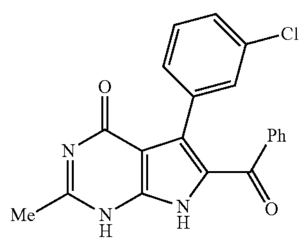 [SMILES: Cc1nc(=O)c2c(-c3cccc(Cl)c3)c(C(=O)c3ccccc3)[nH]c2[nH]1] | 61 | 0.27 ± 0.01 | 0.23 ± 0.00 | 0.90 ± 0.16 | 0.60 ± 0.23 |
| 19 | 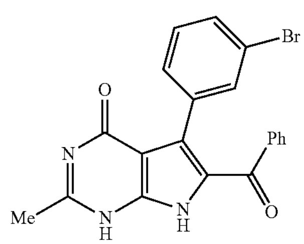 [SMILES: Cc1nc(=O)c2c(-c3cccc(Br)c3)c(C(=O)c3ccccc3)[nH]c2[nH]1] | 40 | 0.29 ± 0.01 | 0.27 ± 0.03 | 0.94 ± 0.12 | 0.65 ± 0.19 |
| 20 | 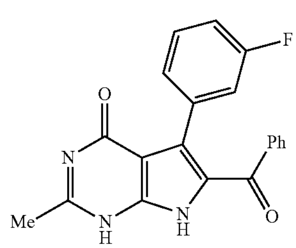 [SMILES: Cc1nc(=O)c2c(-c3cccc(F)c3)c(C(=O)c3ccccc3)[nH]c2[nH]1] | 43 | 0.29 ± 0.03 | 0.36 ± 0.02 | 1.7 ± 0.1 | 1.0 ± 0.9 |

TABLE 6-continued

MCR-based synthesis and antiproliferative activities of C2-methyl-7-deazahypoxanthines 13 and 18-23

| # | structure | % yield | GI$_{50}$ in vitro Values (μM)[a] | | | |
|---|---|---|---|---|---|---|
| | | | HeLa | MCF-7 | U-87 | A549 |
| 21 | 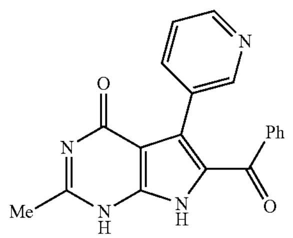 [SMILES: Cc1nc(=O)c2c(-c3cccnc3)c(C(=O)c3ccccc3)[nH]c2[nH]1] | 65 | 3.1 ± 0.1 | 4.7 ± 0.8 | 9.23 ± 2.13 | 12.0 ± 1.4 |
| 22 | 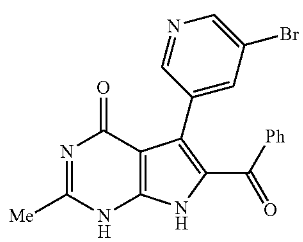 [SMILES: Cc1nc(=O)c2c(-c3cncc(Br)c3)c(C(=O)c3ccccc3)[nH]c2[nH]1] | 63 | 0.49 ± 0.05 | 0.61 ± 0.01 | 2.4 ± 0.6 | 1.1 ± 0.4 |
| 23 | 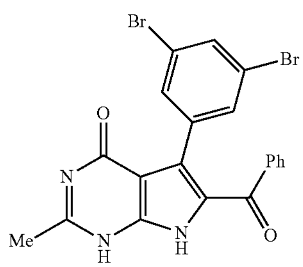 [SMILES: Cc1nc(=O)c2c(-c3cc(Br)cc(Br)c3)c(C(=O)c3ccccc3)[nH]c2[nH]1] | 58 | 0.29 ± 0.01 | 0.27 ± 0.01 | 0.72 ± 0.06 | 0.38 ± 0.08 |

[a]Concentration required to reduce the viability of cells by 50% after a 48 h treatment with the indicated compounds relative to a DMSO control ± SD from two independent experiments, each performed in 4 replicates, as determined by the MTT assay.

The antiproliferative effects of compounds 13 and 18-23 were studied in a more challenging cell line panel that, in addition to the previously utilized HeLa and MCF-7, contained in vitro models for cancers known to be associated with poor prognoses, such as the U-87 human glioblastoma and A549 human non-small-cell lung (NSCLC) carcinoma. Although the newly synthesized compounds 18-23 were found to be inferior to the original C7-phenyl analogue 13, in general the submicromolar potencies were retained with the exception of the pyridine-containing variant 21 exhibiting single-digit micromolar potencies.

(c) Quantitative Videomicroscopy

Poor prognoses of glioblastoma, melanoma and NSCLC patients are generally attributed to the drug resistant nature of these malignanciesand therefore it was encouraging that 7-deazahypoxanthines 13 and 18-23 were active against the U87 human glioblastoma and A549 NSCLC carcinoma cell lines. Since tubulin-targeting agents are generally poorly effective against cancer cells resistant to the induction of apoptosis, compound 22 was further evaluated against U373 human glioblastoma and SKMEL human melanoma cells, reported to display apoptosis resistance. The obtained MTT-based GI$_{50}$ value of 0.3 μM in both of these cell lines indicates that this compound maintains similar levels of activity in these cell types (compare with GI$_{50}$ values in Table 6). Computer-assisted phase-contrast microscopy (quantitative videomicroscopy) was utilized to confirm cell death as the principal mechanism of action associated with this compound's in vitro growth inhibitory effects in these cell lines.

Figure 9:
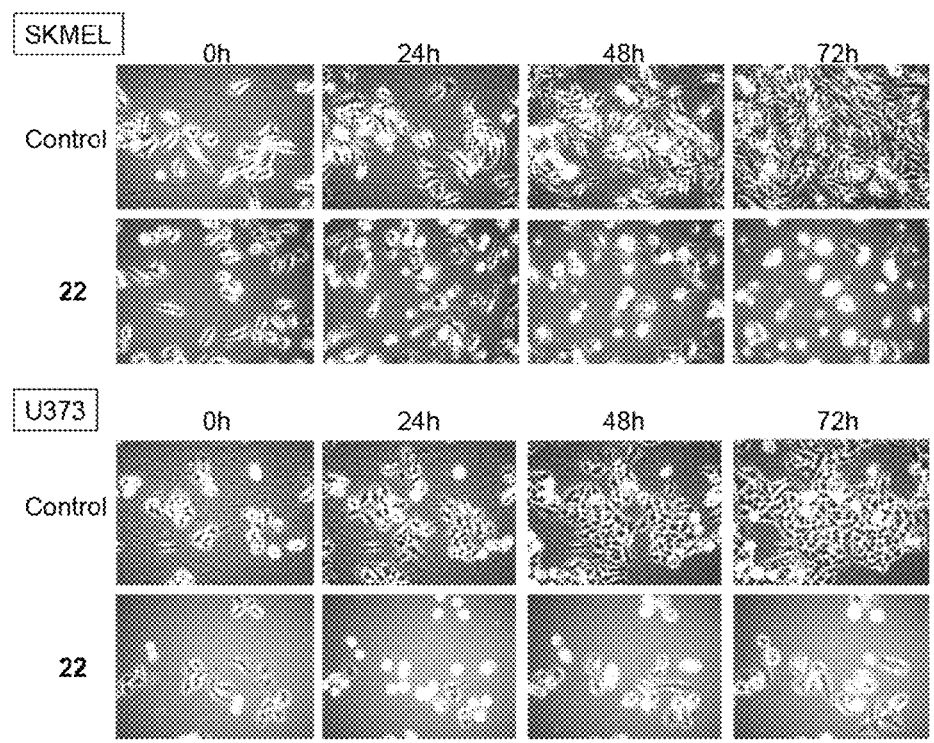
FIG. 9 shows cellular imaging of 22 against U373 glioblastoma and SKMEL melanoma cells illustrating cell death at MTT colorimetric assay-related $GI_{50}$ value of 0.3 μM.

As shown in the cellular imaging below (FIG. 9), 22 indeed inhibited cancer cell proliferation by inducing cell death when assayed at its MTT-based OI$_{50}$ values in U373 glioblastoma and SKMEL melanoma cells.

EXAMPLES

(a) Synthetic Chemistry

All reagents, solvents and catalysts were purchased from commercial sources (Acros Organics and Sigma-Aldrich) and used without purification. All reactions were performed in oven-dried flasks open to the atmosphere or under nitrogen and monitored by thin layer chromatography (TLC) on TLC precoated (250 μm) silica gel 60 F254 glass-backed plates (EMD Chemicals Inc.). Visualization was accomplished with UV light. Flash column chromatography was performed on silica gel (32-63 μm, 60 Å pore size). $^1$H and $^{13}$C NMR spectra were recorded on a Bruker 400 spectrometer. Chemical shifts (δ) are reported in ppm relative to the TMS internal standard. Abbreviations are as follows: s (singlet), d (doublet), t (triplet), q (quartet), m (multiplet). HRMS analyses were performed using Waters Synapt G2 LCMS. The >95% purity of the synthesized compounds was ascertained by UPLC/MS analyses.

Example 1

2-Amino-5-benzoyl-4-phenyl-1H-pyrrole-3-carboxamide (1)

To a stirred solution of N-methylsulfonamidoacetophenone[13] (0.084 g, 0.4 mmol), benzaldehyde (0.055 g, 0.52 mmol) and cyanoacetamide (0.044 g, 0.52 mmol) in EtOH (3 mL) was added anhydrous granulated K$_2$CO$_3$ (0.028 g, 0.2 mmol). The mixture was then refluxed for 14 h. After this time the reaction mixture was cooled to room temperature and concentrated. The crude product was purified by flash chromatography on silica gel using CH$_2$Cl$_2$/AcOEt (2:1) as eluent to obtain 74 mg of the desired pyrrole 1 (61% yield).

Example 2

2-Amino-5-benzoyl-4-phenyl-1H-pyrrole-3-carboxamide (1)

61%; $^1$H NMR (DMSO-d$_6$): δ 10.89 (brs, 1H), 7.18-7.05 (m, 8H), 6.97 (t, J=7.8 Hz, 2H), 6.70 (brs, 1H), 6.39 (s, 2H), 4.59 (brs, 1H); $^{13}$C NMR (DMSO-d$_6$): δ 184.3, 167.6, 149.8, 139.7, 134.6, 132.6, 130.9, 129.9, 128.3, 128.2, 128.0, 127.5, 121.5, 99.4; HRMS m/z (ESI) calcd for C$_{18}$H$_{16}$N$_3$O$_2$ (M+H) 306.1243. found 306.1248.

General procedure for the synthesis of deazahypoxanthines 3-17. A selected ethyl ester (1.28 mmol) and pyrrole 1 (50 mg, 0.16 mmol) were added to the solution of EtONa in EtOH prepared by dissolving sodium metal (30 mg, 1.3 mmol) in EtOH (2 mL). The mixture was then refluxed for 10 h overnight. After that time the reaction mixture was diluted with H$_2$O and neutralized with 1M HCl. The formed precipitate was collected by filtration and dried under vacuum over night. Although in most cases the product deazahypoxanthines were >95% pure, they could be further purified using column chromatography (5% MeOH in CHCl$_3$).

Selected Characterization Data of Compounds in Table 5

Example 3

6-Benzoyl-2-phenyl-5-phenyl-1H-pyrrolo[2,3-d]pyrimidin-4(7H)-one (3)

41%; $^1$H NMR (DMSO-d$_6$): δ 12.21 (brs, 1H), 11.64 (brs, 1H), 8.01-7.96 (m, 2H), 7.74 (t, J=7.3 Hz, 1H), 7.67 (t, J=7.5 Hz, 2H), 7.37-7.09 (m, 10H); $^{13}$C NMR (DMSO-d$_6$): δ 185.8, 167.5, 165.5, 138.4, 133.6, 133.1, 132.6, 131.3, 131.0, 129.8, 129.7, 129.0, 128.7, 128.6, 128.5, 127.9, 127.6, 123.3, 103.4; HRMS m/z (ESI) calcd for C$_{25}$H$_{20}$DN$_4$O$_2$ (M+NH$_4$) 410.1727. found 410.1722.

Example 4

6-Benzoyl-2-(2-ethoxycarbonylethyl)-5-phenyl-1H-pyrrolo[2,3-d]pyrimidin-4(7H)-one (10)

60%; $^1$H NMR (DMSO-d$_6$): δ 12.59 (brs, 1H), 11.91 (brs, 1H), 7.42 (d, J=8.0 Hz, 2H), 7.32 (t, J=8.0 Hz, 1H), 7.20-6.99 (m, 7H), 4.09 (q, J=8.0 Hz, 2H), 2.98-2.75 (m, 4H), 1.15 (t, J=8.0 Hz, 3H); $^{13}$C NMR (DMSO-d$_6$): δ 188.1, 173.9, 172.4, 159.7, 159.6, 158.6, 150.1, 138.0, 133.0, 131.6, 129.5, 128.1, 127.3, 104.9, 60.5, 31.1, 30.4, 14.5; HRMS m/z (ESI) calcd for C$_{24}$H$_{21}$N$_3$NaO$_4$ (M+Na) 438.1430. found 438.1431.

Example 5

6-Benzoyl-2-butyl-5-phenyl-1H-pyrrolo[2,3-d]pyrimidin-4(7H)-one (11)

42%; $^1$H NMR (DMSO-d$_6$): δ 12.54 (brs, 1H), 11.86 (brs, 1H), 7.43 (d, J=6.7 Hz, 2H), 7.30 (t, J=6.8 Hz, 1H), 7.23-6.85 (m, 7H), 2.62 (t, J=6.9 Hz, 2H), 1.81-1.60 (m, 2H), 1.36-1.28 (m, 2H), 0.92 (t, J=7.0 Hz, 3H); $^{13}$C NMR (DMSO-d$_6$): δ 189.1, 160.7, 138.9, 133.9, 133.0, 132.4, 130.3, 128.9, 128.0, 105.6, 35.0, 30.4, 22.9, 14.9; HRMS m/z (ESI) calcd for C$_{23}$H$_{21}$N$_3$NaO$_2$ (M+Na) 394.1531. found 394.1528.

Example 6

6-Benzoyl-2-methyl-5-phenyl-1H-pyrrolo[2,3-d]pyrimidin-4(7H)-one (13)

49%; $^1$H NMR (DMSO-d$_6$): δ 12.57 (brs, 1H), 11.90 (brs, 1H), 7.42 (dd, J=6.7, 0.4 Hz, 2H), 7.31 (t, J=7.4 Hz, 1H), 7.17-7.01 (m, 7H), 2.36 (s, 3H); $^{13}$C NMR (DMSO-d$_6$): δ 188.1, 159.8, 156.8, 150.5, 138.1, 133.0, 132.1, 131.6, 129.5, 128.1, 127.6, 127.4, 127.2, 127.1, 104.7, 21.5; HRMS m/z (ESI) calcd for C$_{20}$H$_{15}$N$_3$NaO$_2$ (M+Na) 352.1062. found 352.1068.

Example 7

6-Benzoyl-2-(difluoromethyl)-5-phenyl-1H-pyrrolo[2,3-d]pyrimidin-4(7H)-one (15)

47%; $^1$H NMR (DMSO-d$_6$): δ 13.12 (brs, 1H), 12.80 (brs, 1H), 7.46 (d, J=7.0 Hz, 2H), 7.35 (t, J=7.4 Hz, 1H), 7.24-7.05 (m, 7H); $^{13}$C NMR (DMSO-d$_6$): δ 188.3, 159.0, 148.2, 137.6, 132.6, 132.5, 131.6, 129.6, 129.2, 128.2, 127.4, 127.0, 112.9, 110.5, 108.1, 106.9; HRMS m/z (ESI) calcd for C$_{20}$H$_{14}$F$_2$N$_3$O$_2$ (M+H) 366.1054. found 366.1054.

Example 8

6-Benzoyl-5-phenyl-2-(trifluoromethyl)-1H-pyrrolo[2,3-d]pyrimidin-4(7H)-one (16)

66%; $^1$H NMR (DMSO-d$_6$): δ 13.34 (brs, 1H), 13.25 (brs, 1H), 7.48 (d, J=7.0 Hz, 2H), 7.36 (t, J=7.4 Hz, 1H), 7.22-7.04 (m, 7H); $^{13}$C NMR (DMSO-d$_6$): δ 188.4, 137.4, 132.8, 132.4, 131.5, 131.3, 131.1, 130.2, 129.6, 129.2, 128.9, 128.3, 128.1, 128.0, 127.5, 127.2; HRMS m/z (ESI) calcd for $C_{20}H_{12}F_3N_3NaO_2$ (M+Na) 406.0779. found 406.0777.

General procedure for the synthesis of deazahypoxanthines 13 and 18-23. To a solution of N-(2-oxo-2-arylethyl)methanesulfonamide (0.676 mmol), the selected aldehyde (0.879 mmol) and cyanoacetamide (0.072 g, 0.879 mmol) in a mixture of EtOH (2.5 mL) and MeC(OEt)$_3$ (2.5 mL) was added anhydrous granulated K$_2$CO$_3$ (0.052 g, 0.372 mmol) in one portion. The mixture was purged with N$_2$ for 5 min and then heated at 90° C. for 24 hours under the nitrogen atmosphere. The formation of the intermediate pyrrole was monitored by TLC. After that the reaction temperature was increased to 150° C., and the reaction mixture was heated for 3-6 h. The mixture was cooled to room temperature, and the formed precipitate was collected by filtration and washed with EtOH (2 mL) and Et$_2$O (2 mL) to give the desired 7-deazahypoxanthine 13 and 17-23. An additional amount of the product was obtained by the evaporation of the mother liquor and purification of the residue by column chromatography with MeOH/CH$_2$Cl$_2$=1/40 to 1/20 gradient.

Characterization Data of Compounds in Table 2

Example 9

6-Benzoyl-5-(3-chlorophenyl)-2-methyl-1H-pyrrolo[2,3-d]pyrimidin-4(7H)-one (17)

61%; $^1$H NMR (DMSO-d$_6$): δ 12.67 (brs, 1H), 11.93 (brs, 1H), 7.44 (d, J=7.2 Hz, 2H), 7.36 (t, J=7.4 Hz, 1H), 7.17 (t, J=7.3 Hz, 2H), 7.13-7.09 (m, 3H), 7.04 (t, J=7.6 Hz, 1H), 2.37 (s, 3H); $^{13}$C NMR (DMSO-d$_6$): δ 187.9, 159.7, 156.9, 150.5, 138.1, 135.2, 132.3, 132.0, 131.2, 130.2, 129.4, 129.0, 128.2, 127.9, 126.9, 125.7, 104.8, 21.5; HRMS m/z (ESI) calcd for $C_{20}H_{15}ClN_3O_2$ (M+H) 364.0853. found 364.0851.

Example 10

6-Benzoyl-5-(3-bromophenyl)-2-methyl-1H-pyrrolo[2,3-d]pyrimidin-4(7H)-one (18)

40%, $^1$H NMR (DMSO-d$_6$): δ 12.67 (brs, 1H), 11.93 (brs, 1H), 7.43 (d, J=7.0 Hz, 2H), 7.36 (t, J=7.5 Hz, 1H), 7.30 (t, J=1.8 Hz, 1H), 7.25-7.15 (m, 4H), 6.99 (t, J=7.8 Hz, 1H), 2.37 (s, 3H); $^{13}$C NMR (DMSO-d$_6$): δ 187.9, 159.7, 157.0, 150.4, 138.1, 135.4, 134.0, 132.3, 130.6, 129.8, 129.3, 129.2, 128.2, 127.9, 125.6, 120.5, 104.8, 21.6; HRMS m/z (ESI) calcd for $C_{20}H_{14}BrN_3NaO_2$ (M+Na) 430.0167. found 430.0168.

Example 11

6-Benzoyl-5-(3-fluorophenyl)-2-methyl-1H-pyrrolo[2,3-d]pyrimidin-4(7H)-one (19)

43%; $^1$H NMR (DMSO-d$_6$): δ 12.66 (brs, 1H), 11.93 (brs, 1H), 7.44 (d, J=7.0 Hz, 2H), 7.35 (t, J=7.4 Hz, 1H), 7.17 (t, J=7.8 Hz, 2H), 7.06-6.99 (m, 2H), 6.94 (dt, J=7.8, 1.2 Hz, 1H), 6.91-6.85 (m, 1H), 2.37 (s, 3H); $^{13}$C NMR (DMSO-d$_6$): δ 187.3, 162.0, 159.6, 159.1, 156.2, 149.8, 137.5, 134.8, 131.6, 128.8, 128.3, 127.5, 127.2, 125.1, 117.6, 113.3, 104.1, 20.9; HRMS m/z (ESI) calcd for $C_{20}H_{14}FKN_3O_2$ (M+K) 386.0707. found 386.0708.

Example 12

6-Benzoyl-2-methyl-5-(pyridin-3-yl)-1H-pyrrolo[2,3-d]pyrimidin-4(7H)-one (20)

65%; $^1$H NMR (DMSO-d$_6$): δ 12.74 (brs, 1H), 11.97 (brs, 1H), 8.30 (dd, J=2.2, 0.7 Hz, 1H), 8.22 (dd, J=4.8, 1.6 Hz, 1H), 7.61-7.57 (m, 1H), 7.47-7.42 (m, 2H), 7.38-7.33 (m, 1H), 7.20-7.14 (m, 2H), 7.07 (ddd, J=7.8, 4.8, 0.8 Hz, 1H), 2.37 (s, 3H); $^{13}$C NMR (DMSO-d$_6$): δ 187.2, 159.4, 156.5, 150.8, 150.2, 147.2, 138.0, 137.5, 131.9, 129.1, 128.7, 127.8, 127.6, 123.2, 121.9, 104.6, 21.1; HRMS m/z (ESI) calcd for $C_{19}H_{14}N_4NaO_2$ (M+Na) 353.1014. found 353.1019.

Example 13

6-Benzoyl-5-(5-bromopyridin-3-yl)-2-methyl-1H-pyrrolo[2,3-d]pyrimidin-4(7H)-one (21)

63%; $^1$H NMR (DMSO-d$_6$): δ 12.90 (s, 1H), 12.09 (s, 1H), 8.36 (d, J=9.0 Hz, 2H), 7.81 (s, 1H), 7.52-7.11 (m, 5H), 2.40 (s, 3H); $^{13}$C NMR (DMSO-d$_6$): 187.6, 159.9, 157.4, 150.7, 150.0, 148.4, 140.8, 138.1, 132.6, 131.2, 129.6, 128.5, 122.2, 119.1, 105.2, 21.7; HRMS m/z (ESI) calcd for $C_{19}H_{14}BrN_4O_2$ (M+H) 409.0300. found 409.0287.

Example 14

6-Benzoyl-5-(3,5-dibromophenyl)-2-methyl-1H-pyrrolo[2,3-d]pyrimidin-4(7H)-one (22)

58%; $^1$H NMR (DMSO-d$_6$) δ 12.82 (s, 1H), 11.94 (s, 1H), 7.48 (s, 1H), 7.44 (d, J=6.0 Hz, 2H), 7.37 (t, J=7.2 Hz, 1H), 7.33 (s, 2H), 7.21 (t, J=6.8 Hz, 2H), 2.28 (s, 3H); $^{13}$C NMR (DMSO-d$_6$): δ 187.9, 160.0, 157.0, 151.1, 138.2, 137.2, 133.2, 132.5, 131.8, 129.2, 128.2, 124.2, 121.1, 104.8, 21.7; HRMS m/z (ESI) calcd for $C_{20}H_{14}Br_2N_3O_2$ (M+H$^+$) 485.9453. found for $C_{20}H_{14}Br_2N_3O_2$ (M+H) 485.9453. found 485.9438.

Example 15

6-Benzoyl-2-(pent-4-ynyl)-5-phenyl-1H-pyrrolo[2,3-d]pyrimidin-4(7H)-one (23)

72%; $^1$H NMR (DMSO-d$_6$) δ 12.57 (brs, 1H), 11.91 (brs, 1H), 7.42 (d, J=7.4 Hz, 2H), 7.30 (t, J=7.4 Hz, 1H), 7.19-6.97 (m, 7H), 2.82 (s, 1H), 2.72 (t, J=6.9 Hz, 2H), 2.28 (t, J=6.8 Hz, 2H), 1.98-1.85 (m, 2H); $^{13}$C NMR (DMSO-d$_6$): δ 187.6, 159.4, 158.8, 149.8, 137.6, 132.6, 131.7, 131.1, 129.0, 127.6, 127.3, 126.8, 126.6, 104.5, 83.8, 71.7, 32.9, 25.7, 17.3; HRMS m/z (ESI) calcd for $C_{24}H_{19}N_3NaO_2$ (M+Na) 404.1375. found 404.1374.

(b) Cell Culture

Human cancer cell lines were obtained from the American Type Culture Collection (ATCC, Manassas, Va., USA), the European Collection of Cell Culture (ECACC, Salisbury, UK) and the Deutsche Sammlung von Mikroorganismen and Zellkulturen (DSMZ, Braunschweig, Germany). Human cervical adenocarcinoma HeLa cells were cultured in DMEM supplemented with 10% fetal bovine serum (FBS). Human mammary carcinoma MCF-7 cells were cultured in RPMI supplemented with 10% FBS. The U87 and U373 cells were cultured in DMEM culture medium (Lonza code 12-136F, Vervier, Belgium), while the SKMEL-28 and A549 cells were cultured in RPMI culture medium (Lonza; code 12-115F) supplemented with 10% heat-inactivated FBS (Lonza, FBS South America code DE14-801F). Cell culture media were supplemented with 4 mM glutamine (Lonza code BE17-605E), 100 µg/mL gentamicin (Lonza code 17-5182), and penicillin-streptomycin (200 units/ml and 200 µg/ml) (Lonza code 17-602E). All cell lines were cultured in T25 flasks, maintained and grown at 37° C., 95% humidity, 5% $CO_2$.

(c) Antiproliferative Properties

To evaluate antiproliferative properties of the synthesized compounds, the MTT assay was used. The cell lines were assessed by trypsinizing each cell line and seeding $4 \times 10^3$ cells per well into 96-well plates. All compounds were dissolved in DMSO at a concentration of either 100 mM or 50 mM prior to cell treatment. The cells were grown for 24 h and then treated with compounds at concentrations ranging from 0.04 to 100 µM and incubated for 48 h in 200 µL media. 20 µL of MTT reagent in serum free medium (5 mg/mL) was added to each well and incubated further for 2 h. Media was removed, and the resulting formazan crystals were re-solubilized in 200 µL of DMSO. $A_{490}$ was measured using a Thermomax Molecular Device plate reader. The experiments were performed in quadruplicate and repeated at least twice for each compound per cell line. Cells treated with 0.1% DMSO were used as a control, and 1 µM phenyl arsine oxide (PAO) was used as a positive killing control.

d) Quantitative Videomicroscopy

The effects of 22 on the viability of human U373 glioblastoma and SKMEL melanoma cells were characterized in vitro using computer-assisted phase contrast video microscopy, as described elsewhere.

The present invention is, of course, in no way restricted to the specific disclosure of the specification and drawings, but also encompasses any modifications within the scope of the appended claims.

What is claimed is:

1. A compound having the formula as follows:

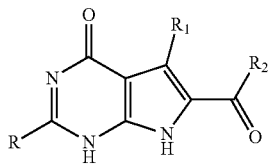

wherein R, $R_1$ and $R_2$ are selected from hydrogen, aryl, fused aryl, heteroaryl, saturated carbocylclic, partially saturated carbocyclic, saturated heterocyclic, partially saturated heterocyclic, $C_{1-10}$ alkyl, haloalkyl, alkenyl, alkynyl, arylalkyl, arylalkenyl, arylalkynyl, heteroarylalkyl, heteroarylalkenyl, alkenylalkyl, alkynylalkyl, carbocycloalkyl, heterocycloalkyl, hydroxyalkyl, aminoalkyl, carboxyalkyl, nitroalkyl, cyanoalkyl, acetamidoalkyl, and acyloxyalkyl.

2. A pharmaceutical composition comprising one or more compounds of the formula of claim 1, as well as pharmaceutically acceptable salts, and/or solvates thereof, and a pharmaceutically acceptable carrier.

3. A method of producing a compound of the formula of claim 1, when R═H or R═Me, including the steps of:
reacting a compound of the Formula II,

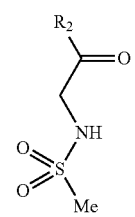

wherein $R_2$ is selected from hydrogen, aryl, fused aryl, heteroaryl, saturated carbocylclic, partially saturated carbocyclic, saturated heterocyclic, partially saturated heterocyclic, $C_{1-10}$ alkyl, haloalkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, and acyloxyalkyl, with a compound of the Formula III,

wherein $R_1$ is selected from hydrogen, aryl, fused aryl, heteroaryl, saturated carbocylclic, partially saturated carbocyclic, saturated heterocyclic, partially saturated heterocyclic, $C_{1-10}$ alkyl, haloalkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, and acyloxyalkyl, in the presence of cyanoacetamide or its synthetic equivalents, and triethyl orthoformate or triethyl orthoacetate, or their synthetic equivalents, as well as a suitable base and solvent, to form one or more compounds of the formula of claim 1.

4. A method of producing a compound of the formula of claim 1, when R≠H and R≠Me, including the steps of:
reacting a compound of the Formula 1,

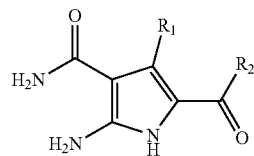

wherein $R_1$ and $R_2$ are selected from hydrogen, aryl, fused aryl, heteroaryl, saturated carbocylclic, partially saturated carbocyclic, saturated heterocyclic, partially saturated heterocyclic, $C_{1-10}$ alkyl, haloalkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, and acyloxyalkyl with a carboxylic ethyl ($RCO_2Et$) or methyl ($RCO_2Me$) ester, wherein R is selected from aryl, fused aryl, heteroaryl, saturated carbocylclic, partially saturated carbocyclic, saturated heterocyclic, partially saturated heterocyclic, $C_{1-10}$ alkyl, haloalkyl, alkenyl, alkynyl, arylalkyl, arylalkenyl, arylalkynyl, heteroarylalkyl, heteroarylalkenyl, alkenylalkyl, alkynylalkyl, carbocycloalkyl, heterocycloalkyl, hydroxyalkyl, aminoalkyl, carboxyalkyl, nitroalkyl, cyanoalkyl, acetamidoalkyl, and acyloxyalkyl in the presence of a suitable base and solvent, to form one or more compounds of the formula of claim 1.

5. A method of treating cervical cancer comprising administering an effective amount of one or more compounds of Formula I.

6. A method of treating lung cancer comprising administering an effective amount of one or more compounds of the formula of claim 1.

7. A method of treating breast cancer comprising administering an effective amount of one or more compounds of the formula of claim 1.

8. A method of treating brain cancer comprising administering an effective amount of one or more compounds of the formula of claim 1.

9. A method of treating melanoma comprising administering an effective amount of one or more compounds of the formula of claim 1.

10. A method of treating colon cancer comprising administering an effective amount of one or more compounds of the formula of claim 1.

11. A method of treating head and neck cancer comprising administering an effective amount of one or more compounds of the formula of claim 1.

12. A method of treating tumor metastases comprising administering an effective amount of one or more compounds of the formula of claim 1.

* * * * *